US 7,336,760 B2

(12) United States Patent
Virshup et al.

(10) Patent No.: US 7,336,760 B2
(45) Date of Patent: Feb. 26, 2008

(54) METHODS, SYSTEMS, AND COMPUTER-PROGRAM PRODUCTS TO ESTIMATE SCATTERED RADIATION IN CONE-BEAM COMPUTERIZED TOMOGRAPHIC IMAGES AND THE LIKE

(75) Inventors: Gary Virshup, Cupertino, CA (US); Roland Suri, Zurich (CH); Edward Seppi, Portola Valley, CA (US); Edward Shapiro, Menlo Park, CA (US); Josh Star-Lack, Palo Alto, CA (US); Erik William Chell, Oakland, CA (US)

(73) Assignee: Varian Medical Systems Technologies, Inc., Palo Alto, CA (US)

( * ) Notice: Subject to any disclaimer, the term of this patent is extended or adjusted under 35 U.S.C. 154(b) by 0 days.

(21) Appl. No.: 11/495,838

(22) Filed: Jul. 28, 2006

(65) Prior Publication Data
US 2008/0025458 A1    Jan. 31, 2008

(51) Int. Cl.
*G01N 23/00* (2006.01)
(52) U.S. Cl. .............................. 378/7; 378/6; 378/207; 378/98.12; 378/901
(58) Field of Classification Search .................... 378/6, 378/7, 98.4, 98.12, 901
See application file for complete search history.

(56) References Cited

U.S. PATENT DOCUMENTS

| 5,666,391 A * | 9/1997 | Ohnesorge et al. ............. 378/7 |
| 5,692,507 A | 12/1997 | Seppi et al. ................ 600/407 |
| 6,173,033 B1 * | 1/2001 | Klingenbeck-Regn et al. ............................ 378/20 |
| 6,789,943 B2 * | 9/2004 | Zapalac ...................... 378/207 |
| 7,190,758 B2 * | 3/2007 | Hagiwara ...................... 378/7 |
| 2004/0120452 A1 | 6/2004 | Shapiro et al. ............... 378/19 |
| 2005/0084060 A1 | 4/2005 | Seppi et al. ................... 378/5 |
| 2005/0147200 A1 * | 7/2005 | Nukui ........................... 378/7 |
| 2005/0185753 A1 * | 8/2005 | Du et al. ....................... 378/7 |

FOREIGN PATENT DOCUMENTS

WO    WO9200566 A1    1/1992

OTHER PUBLICATIONS

J.H. Siewerdsen, et al., "The influence of antiscatter grids on soft-tissue detectability in cone-beam computed tomography with flat-panel detectors," Medical Physics, Dec. 2004, pp. 3506-3520, vol. 31, No. 12, American Association of Physicists in Medicine, College Park, Maryland, USA.

Matthias Bertram, et al., "Potential of software-based scatter corrections in cone-beam volume CT," Medical Imaging 2005: Physics of Medical Imaging. Proceedings of the SPIE, Apr. 2005, pp. 259-270, vol. 5745, The International Society for Optical Engineering, Bellingham WA, USA.

* cited by examiner

*Primary Examiner*—Courtney Thomas
*Assistant Examiner*—Alexander Taningco
(74) *Attorney, Agent, or Firm*—Townsend and Townsend and Crew LLP

(57) ABSTRACT

Disclosed are imaging systems, methods, and computer program products that generate estimates of scattered radiation in tomographic imaging systems, such as cone-beam computerized tomography (CBCT) systems, and the like. In an exemplary embodiment, a first group of projections is taken of an object with the radiation covering a wide band of the object, and a second group of projections is taken of the object with the radiation covering a narrower band of the object. The projections of the second group cover less of the object, but have less scattered radiation. The scattered radiation within the narrower band may be estimated from differences between projections from the first and second groups, or from representations thereof.

47 Claims, 10 Drawing Sheets

Instruction Set #1 directs the data processor to obtain a first group of radiographic projections taken by the two-dimensional imaging device at a corresponding first plurality of angular displacement values; the projections of the first group being taken with radiation from the source incident upon a first band of pixels of the imaging device.

Instruction Set #2 directs the data processor to obtain a second group of radiographic projections taken by the two-dimensional imaging device at a corresponding second plurality of angular displacement values; the projections of the second group being taken with the radiation from the source incident upon at least one second band of pixels of the imaging device, each second band being narrower than the first band; the instruction set further directing the processor to obtain an indication of the number and location of the second bands within each radiographic projection of the second group or to scan each projection of the second group to determine the number and location of the second bands.

Instruction Set #3 directs the data processor to generate a first set of estimates of the scattered radiation (e.g., $ESR_1^1(X,Y,\theta)$) within at least a portion of each second band of pixels for a third plurality of angular displacement values; each estimate of the first set being for a particular angular displacement value of the third plurality and for a particular second band, and comprising a difference between a first representation of the radiographic projection data taken with the source radiation incident upon the first band of pixels and a second representation of the radiographic projection data taken with the source radiation incident upon the particular second band of pixels; the first representation being generated from the at least one radiographic projection of the first group, and the second representation being generated from at least one radiographic projection of the second group.

Instruction Set #4 directs the data processor to generate a second set of estimates of the scattered radiation (e.g., $ESR_1^2(X,Y,\theta)$) within at least a portion of each second band of pixels for the third plurality of angular displacement values; each estimate of the second set comprising a respective estimate of the first set when the respective estimate of the first set is below a truncated value, and each estimate of the second set comprising the truncated value when the respective estimate of the first set is above the truncated value; the estimate of the second group and the respective estimate of the first group being for the same pixel location and for the same angular displacement value.

Instruction Set #5 directs the data processor to generate a third set of estimates of the scattered radiation (e.g., $ESR_1^3(X,Y,\theta)$) for a row of pixels within each second band of pixels for the third plurality of angular displacement values; each estimate of the third set comprising a spatial average of a plurality of estimates of the second set for a particular angular displacement value and particular second band; the estimates for the row of pixels being a row estimate for an angular displacement value and a particular second band.

COMPUTER-READABLE MEDIUM

FIG. 8A

| FIG. 8A |
|---------|
| FIG. 8B |

Instruction Set #6 directs the data processor to assemble, for each second band of pixels, the row estimates of each associated third set of estimates into a respective array (e.g, Sinogram) of a spatial dimension versus angular displacement values, each assembled array (e.g, Sinogram) being a respective fourth set of estimates of the scattered radiation (e.g., $ESR_1^4(X,\theta)$) for the respective second band of pixels; the spatial dimension of the array of each fourth set of estimates corresponding to a first dimension of the two-dimensional imaging device; the imaging device having a second dimension.

Instruction Set #7 directs the data processor to generate, for each second band of pixels, a respective fifth set of estimates of the scattered radiation (e.g., $ESR_1^5(X,\theta)$) in an array form (e.g., Sinogram) of the spatial dimension versus angular displacement values; each fifth set of estimates being generated from the respective fourth set of estimates that was assembled for the same second band of pixels, each estimate of the fifth set being for a pixel in the spatial dimension and an angular displacement value and comprising an average of a plurality of estimates of a respective fourth set that span a plurality of pixels in the spatial dimension and a plurality of pixels in the dimension for angular displacement values.

Instruction Set #8 directs the data processor to obtain an indication of the form in which to generate a sixth set of estimates of the scattered radiation. Each estimate of the sixth set is for all the pixels of the imaging device (in both dimensions) at a particular angular displacement value. If the sixth set of estimates is to be generated in a first form, then execute Instruction Set #9A; if a second form, then execute Instruction Set #9B; if a third form, then execute Instruction Set #9C.

Instruction Set #9A directs the data processor to generate the sixth set of estimates of the scattered radiation (e.g., $ESR_1^6(X,Y,\theta)$) for both dimensions of the imaging device and for the third plurality of angular displacement values, each estimate of the sixth set being for the pixels of the imaging device at a particular angular displacement value and comprising a row of a fifth set of estimates in the spatial dimension for the particular angular displacement value multiplied by a scale function, the scale function being a preset function in the second dimension of the imaging device.

Instruction Set #9B directs the data processor to generate the sixth set of estimates of the scattered radiation (e.g., $ESR_1^6(X,Y,\theta)$) for both dimensions of the imaging device and for the third plurality of angular displacement values, each estimate of the sixth set being for the pixels of the imaging device at a particular angular displacement value and comprising a row of a fifth set of estimates in the spatial dimension for the particular angular displacement value multiplied by a scale function, the scale function being a function in the second dimension of the imaging device; Instruction Set #9B further comprising a subset of instructions that directs the data processor to generate the scale function from the fifth sets of estimates.

Instruction Set #9C directs the data processor to generate the sixth set of estimates of the scattered radiation (e.g., $ESR_1^6(X,Y,\theta)$) for both dimensions of the imaging device and for the third plurality of angular displacement values, each estimate of the sixth set being for the pixels of the imaging device at a particular angular displacement value and being generated from at least one curve-fitting function that has the fifth sets of estimates at the particular angular displacement value as inputs.

COMPUTER-READABLE MEDIUM

*FIG. 8B*

Instruction Set #5A directs the data processor to generate a third set of estimates of the scattered radiation for a row of pixels within each instance of the at least one second band of pixels for the third plurality of angular displacement values, each estimate of the third set comprising a spatial average of a plurality of estimates of the second set for a particular angular displacement value and particular instance of the at least one second band, the estimates of the third set for the row of pixels providing a row estimate for an angular displacement value and a particular instance of the at least one second band, the row estimate being associated with the line location of the particular instance of the at least one second band from which it is generated.

Instruction Set #6A directs the data processor to assemble the row estimates associated with the same line location into a respective array (e.g., Sinogram) of a spatial dimension versus angular displacement values, each assembled array being a respective fourth set of estimates of the scattered radiation for the respective line location, the spatial dimension of the array of each fourth set of estimates corresponding to a first dimension of the two-dimensional imaging device, the imaging device having a second dimension; each fourth set of estimates of the scattered radiation for a respective line location has missing estimated values at a plurality of angular displacement values, and so a preferred embodiment of Instruction Set #6A further comprises instructions that direct the processor to generate the missing estimates by interpolation of estimates at a plurality of other angular displacement values.

Instruction Set #7A directs the data processor to generate, for each line location, a respective fifth set of estimates of the scattered radiation in an array form of the spatial dimension versus angular displacement values, each fifth set of estimates being generated from the respective fourth set of estimates that was assembled for the same line location, each estimate of the fifth set being for a pixel in the spatial dimension and an angular displacement value and comprising an average of a plurality of estimates of a respective fourth set that span a plurality of pixels in the spatial dimension and a plurality of pixels in the dimension for angular displacement values.

COMPUTER-READABLE MEDIUM

METHODS, SYSTEMS, AND COMPUTER-PROGRAM PRODUCTS TO ESTIMATE SCATTERED RADIATION IN CONE-BEAM COMPUTERIZED TOMOGRAPHIC IMAGES AND THE LIKE

FIELD OF THE INVENTION

The present invention relates to tomography, and more particularly to correcting errors caused by extraneous radiation in tomographic systems, such as cone-beam computerized tomography (CBCT) systems, and the like.

BACKGROUND OF THE INVENTION

Cone-beam tomography (CT) involves the imaging of the internal structure of an object by collecting several projection images ("projections") in a single scan operation ("scan"), and is widely used in the medical field to view the internal structure of selected portions of the human body. Typically, several two-dimensional projections are made of the object, and a three-dimensional representation of the object is constructed from the projections using various tomographic reconstruction methods. From the three-dimensional image, conventional CT slices (e.g., cross-sections) through the object can be generated. The two-dimensional projections are typically created by transmitting radiation from a "point source" through the object, which will absorb some of the radiation based on its size and density, and collecting the non-absorbed radiation onto a two-dimensional imaging device, or imager, which comprises an array of pixel detectors (simply called "pixels"). Such a system is shown in FIG. 1. Typically, the point source and the center of the two-dimensional imaging device lie on a common line, which may be called the projection line. The source's radiation generally propagates toward the imaging device in a volume of space defined by a right-circular cone having its vertex at the point source and its base at the imaging device. For this reason, the radiation is often called cone-beam (CB) radiation. A full cone may be projected onto the imaging device, or a half cone may be projected, in which case the center of the imaging device is generally offset from the projection line (the configuration is generally called the half-fan configuration). Generally, when no object is present within the cone, the distribution of radiation is substantially uniform along any perimeter of any circle on the imaging device, with the circle being centered about the projection line and within the cone. However, the distribution of the radiation may be slightly non-uniform among the circle perimeters. In any event, any variation in the distribution can be measured in a calibration step and accounted for.

In an ideal imaging system, rays of radiation travel along respective straight-line transmission paths from the source, through the object, and then to respective pixel detectors without generating scattered rays. However, in real systems, when a quantum of radiation is absorbed by a portion of the object, one or more scattered rays are often generated that deviate from the transmission path of the incident radiation. These scattered rays are often received by surrounding pixel detectors that are not located on the transmission path that the initial quantum of radiation was transmitted on, thereby creating errors in the electrical signals of the surrounding pixel detectors. The collection of scattered rays from all the scattering events that occur during the collection of a projection is referred to herein as the scattered radiation.

The scattered radiation causes artifacts (e.g., phantom images) and loss of resolution and contrast in the CT image slices produced by the radiation imaging system. The size and magnitude of artifacts are generally larger in the half-fan configurations, where the center of the imaging device is offset from the projection line, than in the full-fan configurations. The scattered radiation can also cause numerical errors in the image reconstruction algorithms (generally referred to as "CT number problems" in the art). The foregoing lead to image degradation. Accordingly, there is a need in the cone-beam tomography field to reduce the impacts of scattered radiation.

SUMMARY OF THE INVENTION

The present inventions address the impacts of scattered radiation by estimating the value of the scattered radiation by novel techniques. The estimates may then be subtracted from the measured data, or subtracted out from quantities in the line integrals used by many CT reconstruction algorithms, or otherwise factored out of algorithms used in a CT reconstruction procedure.

A first group of inventions according to the present application is directed to systems that estimate scattered radiation in radiographic projections of an object. An exemplary system comprises a controller, a radiation source, a two-dimensional imaging device disposed opposite the radiation source along a projection line and spaced therefrom to provide a space for the object. The exemplary system has a scan axis that intersects the projection line and to which an object is aligned in a substantially fixed relationship. (The scan axis can be, and often is, perpendicular to the projection line.) In addition, there is a relative rotation between the projection line on the one hand and the scan axis and an object aligned thereto on the other hand, with the relative rotation being measured by an angular displacement value. Various angular displacement values are effected by a rotation of the projection line with respect to the scan axis, a rotation of the object and the scan axis with respect to the projection line, or both such rotations. The imaging device may be centered on the projection line to enable full-fan imaging of the object, may be offset from the projection line to enable half-fan imaging of the object, or may be movable with respect to the projection line to allow both full-fan and half-fan imaging of objects. The imaging device is adapted to measure incident radiation at a plurality of pixels, and is electrically coupled to the controller to provide measured values of the pixels. The configuration enables radiographic projections of the object to be generated, which may thereafter serve as input to a tomographic reconstruction process that enables cross-sectional images of the object along various geometric planes to be generated. The exemplary system further comprises a pair of fan blades disposed between the radiation source and the imaging device, with each fan blade being disposed closer to the radiation source than the imaging device and adapted to attenuate the radiation that strikes it, and preferably to substantially block it. The fan blades may be adapted to move and provide a variable gap between their edges, with their edges being disposed on either side of the plane that contains both of the projection line and the scan axis, or otherwise may be adapted to be selectively moved toward and away from the projection line to provide selective spatial attenuation of rays from the radiation source (in the latter case, the gap between the blades may be fixed). The exemplary system further comprises a gantry that holds the radiation source, the fan blades, and the imaging device in positional relationships to one another. In one exemplary implementation, which is suitable for medical applications, the exemplary system comprises a mechanical drive that is responsive to the controller and that is mechanically coupled to the gantry to enable the components held by the gantry to rotate about the scan axis. In another exemplary implementation, which is suitable for industrial applications, the mechanical drive is responsive to the controller and is mechanically coupled to an object support member to enable the object support member and an object held thereby to rotate within the space between the fan blades and the imaging device. In both implementations, the object support member, the object, and the scan axis on the one hand, and the components held by the gantry on the other hand, rotate relative to one another to provide various angular displacement values.

The controller is adapted to direct the mechanical drive to make at least one scan rotation, and to read a first group of radiographic projections from the imaging device and a second group of radiographic projections. Depending upon the type of reconstruction mode that will be used on the data, a scan rotation may comprise a range of rotation angles from ~200 degrees to 360 degrees. The projections of the first group are taken at a corresponding first plurality of angular displacement values, and are taken with the fan blades set at a first distance apart from one another, or with the fan blades moved away from the projection line, such that the radiation from the source is incident upon a first band (e.g., wide band) of pixels of the imaging device. The projections of the second group are taken at a corresponding second plurality of angular displacement values, and are taken with the fan blades disposed toward the projection line and set at a distance apart from one another such that radiation from the source is incident upon a second band (e.g., narrow band) of pixels of the imaging device. The second band of pixels is narrower than the first band of pixels, and preferably located within the first band of pixels. Thus, the projections of the second group cover less area of the object, but have substantially less scattered radiation. The first and second groups of projections may be taken with the fan blades set at wide and narrow distances, respectively (e.g., first and second distances, respectively, with the second distance being less than the first distance); or with fan blades disposed away from the projection line when the first group of projection is taken, and toward the projection axis and within the radiation field when the second group of projections is taken. From the first and second groups of projections, estimates of the scattered radiation can be generated within at least a portion of the second band of pixels for a plurality of angular displacement values. Each of the estimates comprises a difference between a first representation of the radiographic projection data taken with the source radiation incident upon a first band of pixels and a second representation of the radiographic projection data taken with the source radiation incident upon a second, narrower band of pixels, with the first representation being generated from the at least one radiographic projection of the first group, and the second representation being generated from at least one radiographic projection of the second group. The difference substantially subtracts out the true image data, and leaves a value representative of the scattered radiation. Typically, the first representation is a projection from the first group of projections, and the second representation is a projection from the second group. However, the first representation may comprise an interpolation of data values from two or more projections of the first group, and the second representation may comprise an interpolation of data values from two or more projections of the second group.

A second group of inventions according to the present application is directed to methods that estimate scattered radiation in radiographic projections of an object. An exemplary method comprises the steps of obtaining the above-described first and second groups of radiographic projections, and of estimating the scattered radiation within at least a portion of the second band of pixels for a plurality of angular displacement values from the first and second groups of projections. Each group of projections may be obtained by receiving the projections from an external source, or prompting the generation of the projections by an imaging system. Each of the estimates is generated from a difference between a first representation of the radiographic projection data taken with the source radiation incident upon a first band of pixels and a second representation of the radiographic projection data taken with the source radiation incident upon a second, narrower band of pixels, with the first representation being generated from the at least one radiographic projection of the first group, and the second representation being generated from at least one radiographic projection of the second group. The second band of pixels is preferably located within the first band of pixels.

Additional groups of inventions according to the present application are directed to computer program products that estimate scattered radiation in radiographic projections of an object. One such exemplary computer program product comprises a computer readable medium, a first set of instructions that direct a processor of an imaging system's controller to take a first group of radiographic projections of an object with the source radiation incident upon a first band of pixels, and a second set of instructions that direct the processor to take a second group of radiographic projections of the object with the source radiation incident upon a second, narrower band of pixels. The exemplary computer program may further comprise additional sets of instructions that direct the processor to generate estimates of the scattered radiation from the first and second groups of projections. Another computer program product comprises a computer readable medium, a first set of instructions that direct a processor to receive a first group of radiographic projections of an object with the source radiation incident upon a first band of pixels, a second set of instructions that direct the processor to receive a second group of radiographic projections of the object with the source radiation incident upon a second, narrower band of pixels, and a third set of instructions that direct the processor to generate estimates of the scattered radiation from the first and second groups of projections.

Accordingly, it is an object of several inventions of the present application to estimate the scattered radiation present within the projections used in cone-beam tomography and the like.

It is yet another object of the several inventions of the present application to enable the reduction of image degradation and artifacts in images produced by cone-beam tomography systems and the like.

These and other objects of the present invention will become apparent to those skilled in the art from the following detailed description of the invention, the accompanying drawings, and the appended claims.

BRIEF DESCRIPTION OF THE DRAWINGS

FIG. 8 shown a first exemplary computer program product according to inventions of the present application.

FIG. 9, in combination with portions of FIG. 8, shown a second exemplary computer program product according to inventions of the present application.

DETAILED DESCRIPTION OF THE INVENTION

In the following description, numerous specific details are set forth to provide a more thorough description of specific embodiments of the present inventions. It is apparent, however, that the inventions may be practiced without all the specific details given below. In other instances, well known features have not been described in detail so as to not obscure the inventions. The following table of symbol nomenclature will provide a useful reference for the reader:

R1—number of projections in a first group of radiographic projections;

R2—number of projections in a second group of radiographic projections;

r1—index for the radiographic projections of the first group, r1=1,2, . . . , R1;

r2—index for the radiographic projections of the second group, r2=1,2, . . . , R2;

$\theta$—the angular displacement of the relative rotation between the projection line on the one hand and the scan axis and an object aligned thereto on the other hand, the angular displacement being for the radiographic projections of the first and second groups; as measured in radians, $\theta=2\pi*(r1-1)/R1$ for the first group, and $\theta=2\pi*(r2-1)/R2$ for the second group;

X—the X-coordinate for the two-dimensional imaging device in the X-domain;

Y—the Y-coordinate for the two-dimensional imaging device in the Y-domain;

$Y_{LL}$—the Y-coordinate of the lateral line in the Y-domain of the imaging device;

$F_W$—the spacing distance of the fan blades (i.e., blade gap);

$P_1(X,Y,\theta)$—the measured data of a radiographic projection of the first group;

$P_2(X,Y,\theta,F_W)$—the measured data of a radiographic projection of the second group;

$P_{TRUE}(X,Y,\theta)$—the true image of a projection for coordinate values X and Y of the imaging device taken at an angular displacement of $\theta$.

$SR_1(X,Y,\theta)$—the scattered radiation within the measured data $P_2(X,Y,\theta)$ of the first group;

$SR_2(X,Y,\theta,F_W)$—the scattered radiation within the measured data $P_2(X,Y,\theta,F_W)$ of the second group;

$M(F_W)$—the scatter estimate multiplier;

$M_A(F_W)$—the average scatter estimate multiplier;

$ESR_1^N(X,Y,\theta)$—various estimates for $SR_1(X,Y,\theta)$, where the superscript "N" denotes the different estimates; $ESR_1^N(X,Y,\theta)$ have difference noise and spatial-variation characteristics, and some are not a function of Y.

ASF(Y)—the axial scale factor function, used to construct estimated scatter values for other values of Y based on estimated scatter values on the lateral line ($Y=Y_{LL}$).

Figure 1:
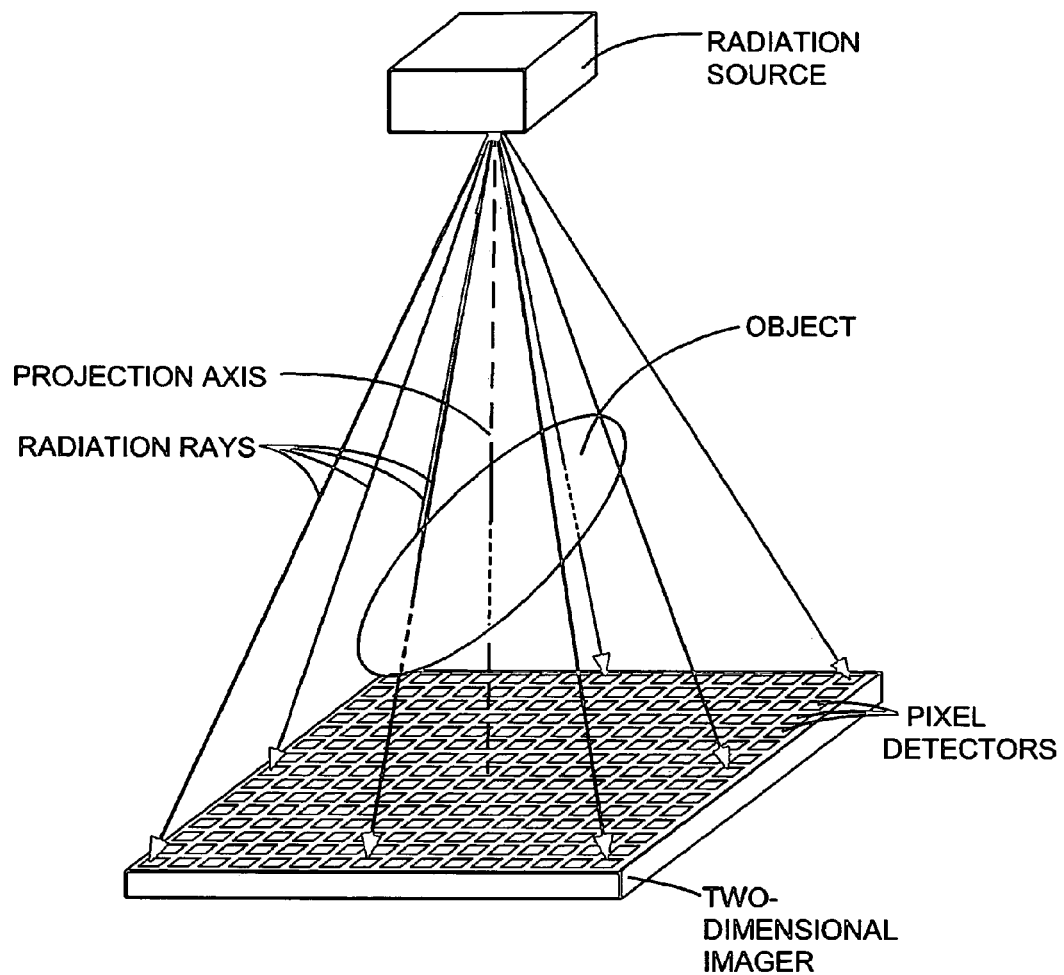
FIG. 1 is a schematic diagram of a radiation imaging system according to the prior art.
Figure 2A:
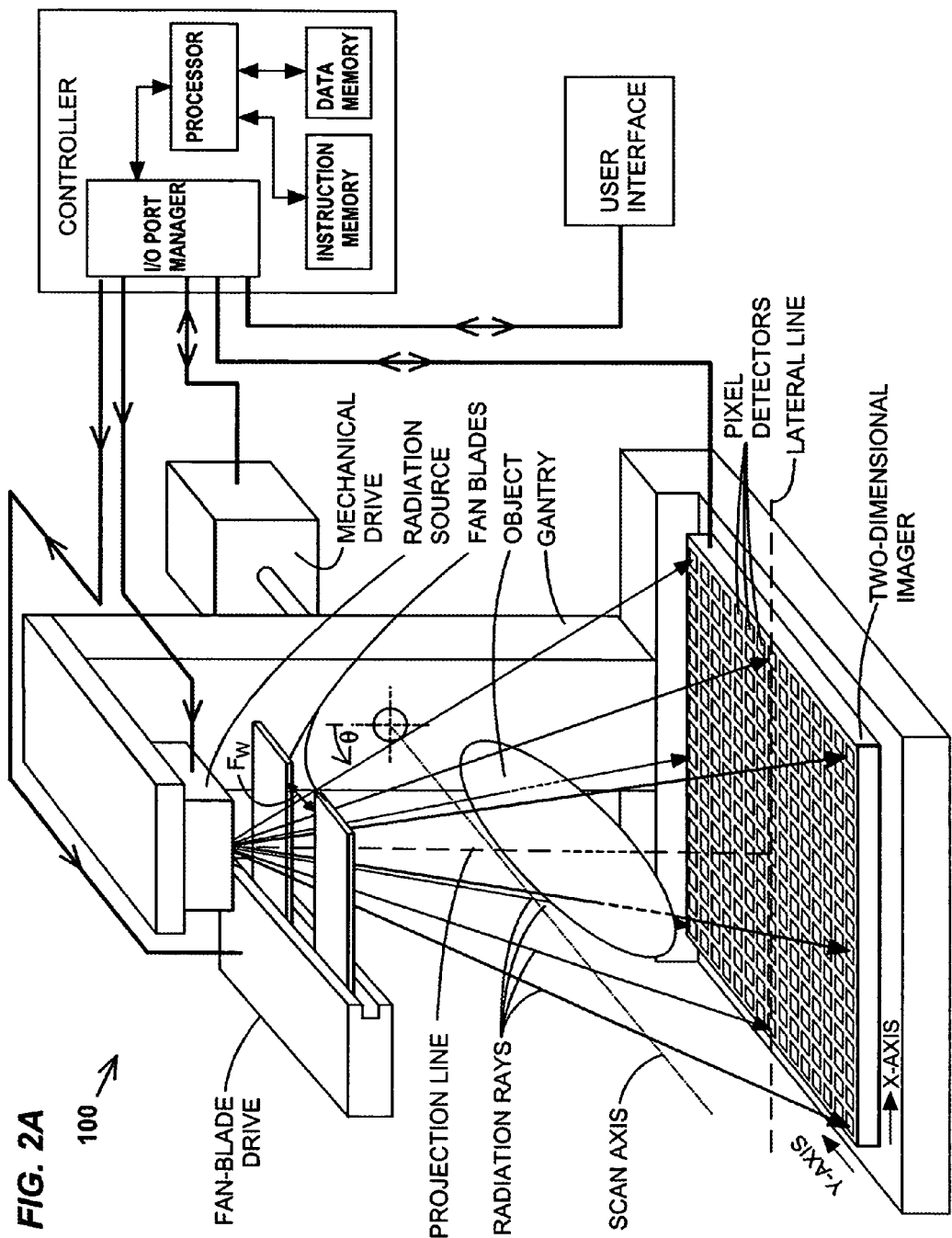
FIG. 2A is a schematic diagram of a first exemplary embodiment of a radiation imaging system according to the present invention.

System Overview. FIG. 2A is a schematic diagram of a first exemplary imaging system 100 according to the systems inventions of the present application. System 100 comprises a radiation source, a two-dimensional imaging device disposed opposite to the radiation source along a projection line, a set of fan blades disposed between the radiation source and the two-dimensional imaging device, and a fan-blade drive that sets the positions of the fan blades. Each fan blade is disposed closer to the source of radiation than the imaging device and is adapted to significantly attenuate the radiation that strikes it, and to preferably substantially block it. System 100 further comprises a gantry that holds the radiation source, imaging device, and fan-blade drive in fixed or known spatial relationships to one another, a mechanical drive that rotates the gantry about an object disposed between the radiation source and the imaging device, the object being further disposed between the fan blades and the imaging device. As used herein, the term fan blades has broad meaning, and covers all configurations of structural members that can provide a primary region (e.g., gap, aperture, etc.) through which radiation may pass with relatively little attenuation compared to one or more surrounding regions, and where a dimension of the primary region may be controlled and/or where the primary region may be selectively disposed toward or away from the projection line so that the primary region can be selectively disposed inside or outside of the source's radiation field that is collected by the imaging device. Additionally, the term gantry has a broad meaning, and covers all configurations of one or more structural members that can hold the above-identified components in fixed or known (but possibly movable) spatial relationships. For the sake of visual simplicity in the figure, the gantry housing, gantry support, and fan-blade support are not shown. These components do not form part of the present inventions. Also not shown is a support table for the object (i.e., an object support member), which does not form a part of present inventions related to System 100. System 100 further comprises a controller and a user interface, with the controller being electrically coupled to the radiation source, the mechanical drive, the fan-blade drive, the imaging device, and the user interface. The user interface provides a human interface to the controller that enables the user to at least initiate a scan of the object, to collect measured projection data from the imaging device, and to generate estimates for the scattered radiation. The user interface may be configured to present graphic representations of the measured data, estimates of the scattered radiation, and the measured data as corrected by the removal of the estimates of the scattered radiation.

In imaging system 100, the gantry is rotated about the object during a scan such that the radiation source, fan blades, fan-blade drive, and the two-dimensional imaging device circle around the object. More specifically, the gantry rotates these components about a scan axis, as shown in the figure, where the scan axis intersects the projection line, and is typically perpendicular to the projection line. The object is aligned in a substantially fixed relationship to the scan axis. The construction provides a relative rotation between the projection line on the one hand and the scan axis and an object aligned thereto on the other hand, with the relative rotation being measured by an angular displacement value $\theta$. The mechanical drive is mechanically coupled to the gantry to provide rotation upon command by the controller. The fan blades are preferably adapted to move and provide a variable gap between their edges, with their edges being disposed on either sides of a plane defined by the projection line and the scan axis (i.e., the plane which contains both the projection line and the scan axis). The two-dimensional imaging device comprises a two-dimensional array of pixels that are periodically read to obtain the data of the radiographic projections. The imaging device has an X-axis and a Y-axis, which are perpendicular to each other. The imaging device is oriented such that its Y-axis is parallel to the scan axis. For later reference, a lateral line on the surface of the imaging device is defined, as shown in the figure. The lateral line is parallel to the X-axis, intersects the projection line, and is given the Y-coordinate of $Y_{LL}$. (Both the X-axis and the lateral line are perpendicular to a plane defined by the scan axis and the projection line, and the edges of the fan blades are parallel to both the X-axis and the lateral line.) Each pixel is assigned a discrete X-coordinate ("X") along the X-axis, and a discrete Y-coordinate ("Y") along the Y-axis. In typical implementations, the size of the array is 1024 pixels by 768 pixels, with the longer dimension of the array being oriented parallel to the X-axis and the lateral line. As used herein, the discrete X-coordinates start at 1 and end at $X_{MAX}$ (e.g., $X_{MAX}=1024$), and the discrete Y-coordinates start at 1 and end at $Y_{MAX}$ (e.g., $Y_{MAX}=768$). The imaging device may be centered on the projection line to enable full-fan imaging of the object, may be offset from the projection line to enable half-fan imaging of the object, or may be movable with respect to the projection line to allow both full-fan and half-fan imaging of objects. As an example of a half-fan configuration, the imaging device may be offset from center by 16 centimeters in its X-dimension when the imaging device has a span in the X dimension of 40 centimeters.

When the controller receives a request from the user to begin a scan of an object, the controller instructs the fan-blade drive to set the fan blades in a given position (as described in greater detail below), instructs the mechanical drive to begin a scan rotation of the gantry, and instructs the radiation source to begin emitting radiation. As it rotates, the mechanical drive provides the controller with an indication of the angular displacement value $\theta$. The controller uses this information to read the values of the imaging device's pixel detectors at selected angular displacement values $\theta$ to obtain the data for the radiographic projections. Typically, there are between 250 and 1000 projections taken in the 360-degree scan rotation, with each projection being spaced from adjacent projections by a set increment $\Delta\theta$ of angular displacement. The controller stores the data from each projection in a memory storage device, along with the angular displacement value $\theta$ at which the projection was taken.

The controller comprises a processor, an instruction memory for storing instruction sets that direct the operation of the processor, a data memory that stores pixel and other data values used by the present inventions implemented by the imaging system, and an I/O port manager that provides input/output data exchange between the processor and each of the radiation source, the mechanical drive, the fan-blade drive, and the imaging device. The instruction memory and data memory are coupled to the main processor through a first bidirectional bus, and may be implemented as different sections of the same memory device. Because of the large amount of data provided by the two-dimensional imaging device, the I/O port manager is preferably coupled to the main processor through a second bidirectional bus. However, the I/O port manager may be coupled to the main processor by way of the first bidirectional bus. The operation of the processor is guided by a group of instruction sets stored in the instruction memory, which is an exemplary form of computer-readable medium. Exemplary instruction sets are illustrated below.

In exemplary imaging system 100 shown in FIG. 2A, the gantry rotates about the object, which means that the projection line rotates about the object and the scan axis. Instead, it may be appreciated that the object and the scan axis may be rotated while the gantry and the projection line are stationary. A second exemplary imaging system which rotates the object is shown at 100' in FIG. 2B. System 100' comprises all of the components of system 100, with the components being coupled to one another in the same way, except that the mechanical drive is coupled to an object support member, which holds the object being scanned. In system 100', the gantry remains stationary while the mechanical drive rotates the object support member and the object. System 100' is suitable for industrial uses (e.g., scanning non-human objects), whereas system 100 is suitable for medical uses (e.g., scanning human objects).

Collection of Data. In preferred embodiments of the present inventions, a first group of radiographic projections of the object is obtained from the two-dimensional imaging device during a scan operation with the fan blades set at a distance far apart from one another (e.g., fully open), or disposed away from the projection line and outside of the source's radiation that strikes the imaging device, thereby enabling the source radiation to project upon a first band of pixels of the imaging device (e.g., the full pixel array). (Either of systems 100 or 100' may be used for this.) The first group typically has 250 to 1000 projections, the total number being denoted herein as R1, with each of the projections containing wide-area image information about the object as well as scattered radiation. In preferred embodiments, the number R1 of projections of the first group ranges from 600 to 690, and the projections are spaced apart from one another at equally spaced intervals of angular displacement $\theta=2\pi(r1-1)/R1$ (in radians), where r1 is the index for the radiographic projections of the first group, $r1=1,2,\ldots,R1$. The measured data of a radiographic projection of this first group is denoted herein as $P_1(X,Y,\theta)$.

Next, a second group of radiographic projections of the object is obtained from the two-dimensional imaging device during a scan operation with the fan blades set at a distance close to one another but still separated (e.g., nearly closed), and disposed toward the projection line and within the source's radiation that strikes the imaging device. (Either of systems 100 or 100' may be used for this.) This enables the source radiation to project upon a second, narrower band of pixels of the imaging device, such as a band that is approximately 100 pixels wide along the Y-axis, and causes significantly less scattered radiation to be present in the radiographic projection. (By comparison, the first band described above typically has a width of 768 pixels.) The second band is preferably located within the first band. The second group of projections has the same or fewer number of projections as the first group, with each projection of the second group covering less area of the object. Typically, each projection of the second group is taken with the same angular displacement value $\theta$ as a corresponding projection of the first group. (However, as indicated below, this is not a requirement of the inventions.) The number of projections in the second group, which is denoted herein as R2, can be as low as eight (8) for human objects, and possibly lower for other types of objects. In preferred embodiments, the number R2 of projections in the second group is an integral fraction of the number in the first group, such that R2=R1/u, where typically u is within the set $\{2, 3, \ldots R\frac{1}{4}\}$. As in the case of the first group, the projections are spaced apart from one another in equal increments of angular displacement $\theta=2\pi*(r2-1)/R2$ (in radians), where r2 is the index for the radiographic projections of the second group, r2=1,2, . . . , R2. The measured data of a radiographic projection of the second group is denoted herein as $P_2(X,Y,\theta,F_W)$, where $F_W$ is the distance between the blades, called blade gap herein.

In one set of embodiments, two separate scans are performed to generate the first and second groups of radiographic projections. Preferably, the scan of the second group is done first, so that the results can be used during the scan of the first group to estimate the scattered radiation substantially in real time, and to factor the scattered radiation out of the results of the first group of radiographic projections so that the user can see corrected projections of the first group substantially in real time. It also allows an image reconstruction process (needed for producing CT cross-section slices as opposed to two-dimensional projections) to be started shortly after the first scan begins, thereby allowing the reconstruction process to overlap with the scatter estimation process. (Here, "real time" means that the projections in the first group are processed as they are received to generate estimated values of the scattered radiation, generally with the initial projections being processed before the scan has finished; and that corrected projections of the first group are generated as the scatter-radiation estimates are generated for the corresponding uncorrected projections.)

In another set of embodiments where R2 is a low number (such as 32 or less), one scan is performed with the fan blades being periodically moved to the second spacing distance (narrow distance) to generate a second projection. For example, taking R2=R1/u, an exemplary scan is started with the fan blades set first to the second distance to take the first projection of the second group. The fan blades are then moved to the first spacing distance (wide distance), and the gantry or the object is rotated to collect the first number "u" of the first group of projections. The rotation is then stopped, and the blades are moved in to collect the second projection of the second group. The fan blades are then moved out, and the rotation is started again to collect the next number "u" of projections in the first group. These latter steps are then repeated several times until the rotation goes the angles needed for image reconstruction and all of the projections have been collected. It can typically take two seconds to stop the rotation, move the fan blades in, collect a projection, and move the fan blades back out, before restarting the rotation. Thus, collection of sixteen (16) projections for the second group (R2=16) in this embodiment would add about 30 seconds to the scan time.

As indicated above, it is not a requirement of the present inventions that each projection of the second group is taken with the same angular displacement value $\theta$ as a corresponding projection of the first group. As an example, a single scan with continuous rotation of the gantry or object may be used to collect the first and second groups of projections, with a second projection being collected between each number "u" of first projections. Different constructions for the fan blades and fan-blade drive may be used in order to increase the speed at which the blade gap may be changed, or the speed at which the blade gap may be moved in and out of the source's radiation field that strikes the imaging device. Because of the continuous movement, there are no projections in the first group having the same angular displacement values as the second group of projections. However, a pseudo-projection, or imaginary projection, may be generated by interpolation to serve as a replacement to each such "missing" projection of the first group. The interpolation may be based on conventional interpolation methods, and may use the two projections of the first group which have angular displacement values that are closest to that of the missing projection. Techniques to account for the rotation about the object may be included in the interpolation.

Generation of Estimates of the Scattered Radiation. Once the first and second groups of radiographic projections have been collected, pixel data from each projection in the second group can be subtracted from the corresponding pixel data in the first group to generate values representative of the scattered radiation at the corresponding pixel locations. As described below in greater detail, these values can be processed to generate estimates of the scattered radiation over the entire X-Y domain of the two-dimensional imaging device for each of the projections of the first group, and the estimated scattered radiation can then be subtracted from the radiographic projections of the first group to generate a group of correct radiographic projections from which CT cross-sections of the object can be generated. The group of corrected radiographic projections reduces the artifacts within the CT cross-sections.

Mathematical Framework. The process is now described in greater detail, starting with the mathematical framework. Each projection $P_1(X,Y,\theta)$ of the first group comprises the true image projection, which is denoted herein as $P_{TRUE}(X,Y,\theta)$, plus the scattered radiation, which is denoted herein as $SR_1(X,Y,\theta)$. This can be written mathematically as:

$$P_1(X,Y,\theta)=P_{TRUE}(X,Y,\theta)+SR_1(X,Y,\theta) \quad [1]$$

A similar mathematical relation may be written for each projection $P_2(X,Y,\theta,F_W)$ of the second group:

$$P_2(X,Y,\theta,F_W)=\Pi(\alpha \cdot Y/F_W-Y_{LL}) \cdot P_{TRUE}(X,Y,\theta)+SR_2(X,Y,\theta,F_W) \quad [2]$$

where $\Pi(\alpha \cdot Y/F_W-Y_{LL})$ is a rectangle function that accounts for the spatial modulation of the source radiation caused by the fan blades, $F_W$ is the spacing distance of the fan blades (i.e., blade gap), $\alpha$ is a scaling factor that accounts for the enlargement of the blade gap as it is projected from the fan blades to the two-dimensional imaging device, $Y_{LL}$ is the Y-offset distance to the lateral line, and $SR_2(X,Y,\theta,F_W)$ is the scattered radiation in the projections of the second group. Rectangle function $\Pi(*)$ has an output value of 1 for input values between $-\frac{1}{2}$ and $+\frac{1}{2}$, and an output value of zero elsewhere. In reality, a soft rectangle function with shaped side edges (at input values of $-\frac{1}{2}$ and $+\frac{1}{2}$) should be used instead of a hard rectangle function $\Pi(*)$ in order to account for the point-spreading effects at the radiation source. However, preferred embodiments process the pixel data well within the interior of the rectangle function and there is no need to accurately model the side regions.

The scatter function $SR_2(X,Y,\theta,F_W)$ in formula [2] is different from the scatter function $SR_1(X,Y,\theta)$ in formula [1] principally because the fan blades substantially eliminate the scattered radiation that would have been generated by the portions of the object that are shadowed by the fan blades. The characteristics of the eliminated scattered radiation depend upon the blade gap $F_W$ and the object being imaged, but reasonable bounds on its effects can be empirically determined or modeled (e.g., computationally simulated). For the purposes of presenting a mathematical framework, $SR_2(X,Y,\theta,F_W)$ can be approximately related to $SR_1(X,Y,\theta)$ by the following formula:

$$SR_2(X,Y,\theta,F_W) \approx \cap(\alpha'\cdot Y/F_W - Y_{LL}, F_W)\cdot H(F_W)\cdot SR_1(X,Y,\theta) \quad [3]$$

where $\cap(\alpha'\cdot Y/F_W - Y_{LL}, F_W)$ is a soft trapezoidal function that accounts for the spatial modulation of the source radiation caused by the fan blades and the elimination of scattered radiation from the regions of the object shadowed by the fan blades, $F_W$ is the spacing distance of the fan blades (i.e., blade gap), $\alpha'$ is a scaling factor that accounts for the enlargement of the blade gap between the shadowed regions of the object as it is projected onto the two-dimensional imaging device, $Y_{LL}$ is the Y-offset distance to the lateral line, and $H(F_W)$ is a height function that accounts for the overall reduction of the scattered radiation caused by the fan blades. As the spacing distance $F_W$ of the blades decreases, the height function $H(F_W)$ approaches zero; and as $F_W$ increases to its wide-open position, the height function $H(F_W)$ approaches unity. $\Omega(*)$ has an output value of 1 for input values of 0 and a portion thereabout, decreasing to values of ½ at input values –½ and +½, with values decreasing to zero to the sides of –½ and +½. Substituting formula [3] into formula [2], and thereafter taking the difference with formula [1], the following relation can be obtained:

$$P_1(X,Y,\theta) - P_2(X,Y,\theta,F_W) \approx P_{TRUE}(X,Y,\theta)\cdot\{1 - \Pi(\alpha\cdot Y/F_W - Y_{LL})\} +$$

$$SR_1(X,Y,\theta)\cdot\{1 - \cap(\alpha'\cdot Y/F_W - Y_{LL}, F_W)\cdot H(F_W)\} \quad [4]$$

Within the region where both $\Pi(\alpha\cdot Y/F_W - Y_{LL})$ and $\cap(\alpha\alpha\cdot Y/F_W - Y_{LL}, F_W)$ are equal to 1, which can be defined as $(Y_{LL} - \Delta Y/2) \leq Y \leq (Y_{LL} + \Delta Y/2)$, formula [4] simplifies to:

$$P_1(X,Y,\theta) - P_2(X,Y,\theta,F_W) \approx SR_1(X,Y,\theta)\cdot\{1 - H(F_W)\} \quad [5]$$

Typically, $\Delta Y$ may be around 30 pixels when the projection of the blade gap $F_W$ onto the two-dimensional imaging device is around 100 pixels wide. Formula [5] may be used to estimate the scattered radiation within the narrow Y band from $(Y_{LL} - \Delta Y/2)$ to $(Y_{LL} + \Delta Y/2)$ as follows:

$$SR_1(X,Y,\theta) \approx \{1 - H(F_W)\}^{-1}\cdot\{P_1(X,Y,\theta) - P_2(X,Y,\theta,F_W)\} \quad [6]$$

$$\approx M(F_W)\cdot\{P_1(X,Y,\theta) - P_2(X,Y,\theta,F_W)\}$$

where the quantity $\{1 - H(F_W)\}^{-1}$ is designated herein as the scatter estimate multiplier $M(F_W)$ for simplicity.

Since the height function $H(F_W)$ depends upon the blade gap $F_W$ and the characteristic of the object, multiplier $M(F_W)$ also depends upon these factors. By taking measurements on a calibrated phantom that is representative of the objects that will normally be measured (e.g., human torso regions, head regions), or by using Monte Carlo simulation techniques to simulate such measurements, the dependency of multiplier $M(F_W)$ on these factors can be estimated (in this case, $P_{TRUE}(X,Y,\theta)$ is known for the phantom). More specifically, the phantom can be measured (or simulated by Monte Carlo techniques) at several different angular displacement values $\theta$ and at several different values of blade gap $F_W$ to find $P_1(X,Y,\theta)$ and $P_2(X,Y,\theta,F_W)$, and a known scattered radiation data set $SR_1^*(X,Y,\theta)$ can be computed from $P_1(X,Y,\theta)$ and $P_{TRUE}(X,Y,\theta)$. The value of the multiplier $M(*)$ at various values of $X$, $Y$, $\theta$ within the narrow Y band from $(Y_{LL} - \Delta Y/2)$ to $(Y_{LL} + \Delta Y/2)$ can be estimated according to the formula:

$$M(X,Y,\theta,F_W) = \{P_1(X,Y,\theta) - P_2(X,Y,\theta,F_W)\}/SR_1^*(X,Y,\theta) \quad [7]$$

Figure 3:
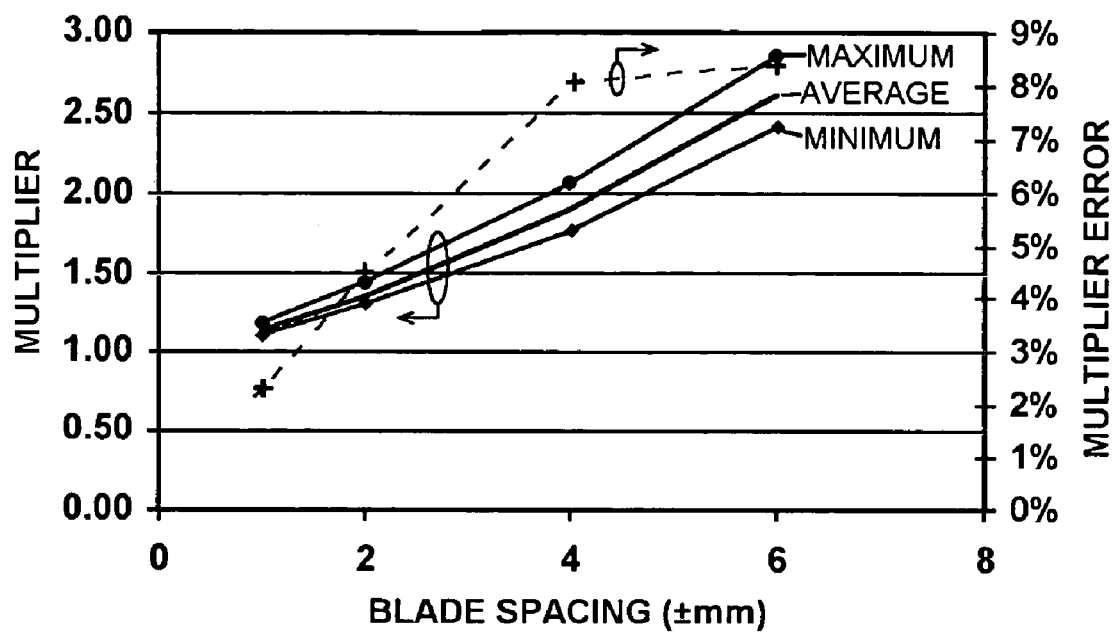
FIG. 3 is a graph of minimum, maximum, and average values of the scatter estimate multiplier, and of the associated multiplier error, according to inventions of the present application.

These values may be analyzed for a minimum value, a maximum, and an "average" value at each of the test values of blade gap $F_W$, and plotted as shown in FIG. 3 for blade gap values of 2 mm, 4 mm, 8 mm, and 12 mm (the X-axis in this figure is given in the spacing distance of each blade from a center line, where this spacing distance is one-half the value of the blade gap $F_W$). Here, the term "average" has broad meaning where the "average" value can be computed as a mean, a median, a strict average, or as any other conventional central tendency value. The data can be further analyzed to find the error that would be caused if the "average" value were used for all of the data at a given value of blade gap $F_W$. This error, which is called the "multiplier error," is plotted as the dashed line in FIG. 3. The error ranges from approximately 2.3% for $F_W=2$ mm, to approximately 8.5% for $F_W=12$ mm. Since this error is relatively small, an "average" value of the multiplier $M(X,Y,\theta,F_W)$ can be used for all the measured data at a given blade gap $F_W$. The "average" multiplier value is denoted herein as $M_A(F_W)$. While the use of smaller values of blade gap $F_W$ results in minimal multiplier error, the measurement of $P_2(X,Y,\theta,F_W)$ becomes more noisy as the blade gap value $F_W$ decreases. The inventors have found that a blade gap value of $F_W=4$ mm represents a good compromise between the error caused by noise in $P_2(X,Y,\theta,F_W)$ and the multiplier error, which is approximately 4.5% at $F_W=4$ mm. Thus, within the narrow Y band from $(Y_{LL} - \Delta Y/2)$ to $(Y_{LL} + \Delta Y/2)$, the scattered radiation $SR_1(X,Y,\theta)$ can be estimated by the formula:

$$SR_1(X,Y,\theta) \approx M_A(F_W)\cdot\{P_1(X,Y,\theta) - P_2(X,Y,\theta,F_W)\} \quad [8A]$$

where $M_A(F_W)$ is taken from FIG. 3, or otherwise generated by the exemplary steps outlined above, which may be carried out by one of ordinary skill in the art in view of the present disclosure without undue experimentation. Steps that reduce the noise in the estimate for $SR_1(X,Y,\theta)$ and that extrapolate the estimate to values of Y outside of the narrow band from $(Y_{LL} - \Delta Y/2)$ to $(Y_{LL} + \Delta Y/2)$ are described below in greater detail. To facilitate this description, we introduce the notation $ESR_1^N(X,Y,\theta)$ to denote various estimates for $SR_1(X,Y,\theta)$, where the superscript "N" denotes different estimates, having different noise and spatial-variation characteristics. Some of the estimates $ESR_1^N(X,Y,\theta)$ are not a function of Y. We also define the right-hand side of formula [8A] as the first estimate (N=1) in the series:

$$ESR_1^1(X,Y,\theta) = M_A(F_W)\cdot\{P_1(X,Y,\theta) - P_2(X,Y,\theta,F_W)\} \quad [8B]$$

While one example of scatter multiplier $M_A(F_W)$ has been used to illustrate the mathematical framework, it may be appreciated that different scatter multipliers may be constructed (as described above) for different types of objects.

Data Conditioning Prior to Low-Pass Filtering. Because the scattered radiation slowly varies in value in the X- and Y-dimensions (i.e., it has low spatial frequencies), estimates of the scattered radiation can be low-pass filtered in the spatial dimensions to reduce the errors caused by noise in the projection data. The filtering can be done in a number of ways, such as using a two-dimensional averaging window over the values generated from formula [8B]. However, typically, there is a large change in $SR_1(X,Y,\theta)$ (and $ESR_1^{\ 1}(X,Y,\theta)$) at the edge of the object which can degrade the benefits of low-pass filtering near the object's edges. The inventors have discovered that low-pass filtering can be made more effective at the object's edges by first conditioning the data provided in $ESR_1^{\ 1}(X,Y,\theta)$ before low-pass filtering the data. (While the conditioning is preferred, it is not essential to practicing the present inventions.) In preferred embodiments, the discrete X-coordinates of the object's edges are found in the narrow band ($Y_{LL}-\Delta Y/2$ to $Y_{LL}+\Delta Y/2$) of $ESR_1^{\ 1}(X,Y,\theta)$ for a sample projection $\theta=\theta_S$ in the first group (e.g., $\theta_S=\theta$), and a maximum value of $ESR_1^{\ 1}(X,Y,\theta_S)$ within the object's interior area is thereafter found, the maximum value being called the "maximum interior value" for clarity. The discrete X-coordinates of the object's edges along the lateral line may be found by finding the points of steepest change in $ESR_1^{\ 1}(X,Y,\theta_S)$ with respect to the discrete X-coordinates along the lateral line ($Y=Y_{LL}$). A truncated value is then generated from the maximum interior value, such that the truncated value is less than the maximum value outside of the object's interior area, but larger than the maximum interior value. Typically, the truncated value is between two and three times the maximum interior value, with a factor of 2.5 times being exemplary. Next, for each projection, a second estimate $ESR_1^{\ 2}(X,Y,\theta)$ is generated from $ESR_1^{\ 1}(X,Y,\theta)$, with the values corresponding to the object's interior area being copied from $ESR_1^{\ 1}(X,Y,\theta)$ and the values outside of the object interior area being set equal to a truncated value. This conditions the data by reducing the step height in the values of $ESR_1^{\ 2}(X,Y,\theta)$ at the edges of the object, and the reduced step height minimizes the loss of resolution and accuracy at the edges when low-pass filtering is subsequently done. After this conditioning step, low-pass filtering may be done using the data in $ESR_1^{\ 2}(X,Y,\theta)$ to provide a third estimate $ESR_1^{\ 3}(X,Y,\theta)$.

An exemplary implementation of the above processing is now described. First, a relatively small amount of low-pass filtering can be done on the data provided by $ESR_1^{\ 1}(X,Y,\theta_S)$ of a sample projection ($\theta=\theta_S$) in order to reduce the noise in the data before finding the points of steepest change in $ESR_1^{\ 1}(X,Y,\theta_S)$ with respect to the discrete X-coordinates along the lateral line ($Y=Y_{LL}$). For this, a moving two-dimensional averaging window (equal weighting) may be applied to the data in $ESR_1^{\ 1}(X,Y,\theta_S)$, the results of which can be equivalent to the following mathematical formula:

$$ESR_1^{T2}(X, Y_{LL}, \theta_S) = \frac{1}{N_X \cdot N_Y} \cdot \sum_{x=X-\frac{1}{2}\Delta X}^{X+\frac{1}{2}\Delta X} \sum_{y=Y_{LL}-\frac{1}{2}\Delta Y}^{Y_{LL}+\frac{1}{2}\Delta Y} ESR_1^1(x, y, \theta_S) \quad [9]$$

for each discrete X of the sample projection $\theta=\theta_S$ (with $Y=Y_{LL}$), where $N_Y$ is the number of pixels used in the summation of $ESR_1^{\ 1}(X,Y,\theta)$ over the Y-dimension, and where $N_X$ is the number of pixels used in the summation of $ESR_1^{\ 1}(X,Y,\theta)$ over the X-dimension. In one exemplary embodiment, $N_Y$ is approximately 10 to 20 pixels (which span distance $\Delta Y$), and $N_X$ is on the order of one to five pixels (which span distance $\Delta X$). The superscript "T2" has been used in $ESR_1^{\ T2}(X,Y_{LL},\theta_S)$ to indicate that this is a temporary set of estimated scatter values generated to aid in finding the object's edge along the lateral line in the sample projection and in generating the second above-described estimate $ESR_1^{\ 2}(X,Y_{LL},\theta)$. Note that $ESR_1^{\ T2}(X,Y_{LL},\theta_S)$ is only generated along the lateral line (i.e., the Y-coordinate has been set to $Y_{LL}$). Next, $ESR_1^{\ T2}(X,Y_{LL},\theta_S)$ is examined along the lateral line to find the point of steepest change with respect to the discrete X-coordinates. For this, successive values of $ESR_1^{\ T2}(X,Y_{LL},\theta_S)$ along the discrete X-coordinates can be examined to find the largest difference. As an example, the following set of difference formulas may be used:

$$Diff(X,Y_{LL},\theta_S)=ESR_1^{T2}(X+xp,Y_{LL},\theta_S)-ESR_1^{T2}(X-xp,Y_{LL},\theta_S), \quad [10A]$$

$$Diff(X,Y_{LL},\theta_S)=ESR_1^{T2}(X+2xp,Y_{LL},\theta_S)-ESR_1^{T2}(X-2xp,Y_{LL},\theta_S) \quad [10B]$$

where xp is the distance between two adjacent pixels in the X-axis. Formula [10B] uses a wider difference base (2xp versus xp) than formula [10A], and is less prone to the effects of noise. Formulas similar to the above having wider differences can also be used. Also, the above forms may be applied directly to $ESR_1^{\ 1}(*)$ rather than $ESR_1^{\ T2}(*)$. The examined slices of $ESR_1^{\ T2}(*)$ can have one or both of the left and right edges of the object, but typically only have one of the edges. In general, if it exists in the radiographic projection and in $ESR_1^{\ T2}(*)$, the left edge of the object can be found by finding the value of X at which $Diff(X,Y_{LL},\theta_S)$ has its largest negative value that is closest to $X=1$ and that is above a predetermined threshold amount. This value of X may be selected as the left edge, or a value of X that is 5 to 20 pixels toward the object's interior area may be selected as the left edge to account for fringing effects around the left edge. Similarly, if it exists in the radiographic projection and in $ESR_1^{\ T2}(*)$, the right edge of the object can be found by finding the value of X at which $Diff(X,Y_{LL},\theta_S)$ has its largest positive value that is closest to $X_{MAX}$ and that is above a predetermined threshold amount. This value of X may be selected as the right edge, or a value of X that is 5 to 20 pixels toward the object's interior area may be selected as the right edge to account for fringing effects around the right edge. Once the left and/or right edges have been found, the maximum interior value may be readily found, and the truncated value generated from the maximum interior value, as described above.

A second set of estimated scatter values $ESR_1^{\ 2}(X,Y,\theta)$ may then be generated by setting the values of $ESR_1^{\ 2}(X,Y,\theta)$ equal to the corresponding values of $ESR_1^{\ 2}(X,Y,\theta)$, except for those values of $ESR_1^{\ 1}(X,Y,\theta)$ that exceed the truncated value, in which case the corresponding values of $ESR_1^{\ 2}(X,Y,\theta)$ are set equal to the truncated value. This may be mathematically stated by the following formula:

$$ESR_1^{\ 2}(X,Y,\theta)=Trunc(ESR_1^{\ 1}(X,Y,\theta), \text{truncated value}), \quad [11]$$

for each discrete X, each discrete $\theta$, and each discrete Y in the band from ($Y_{LL}-\Delta Y/2$) to ($Y_{LL}+\Delta Y/2$), where Trunc(*) is the mathematical truncation function. Like the first scatter estimate $ESR_1^{\ 1}(X,Y,\theta)$, the second estimate $ESR_1^{\ 2}(X,Y,\theta)$ only has values for discrete Y-coordinates in the band from ($Y_{LL}-\Delta Y/2$) to ($Y_{LL}+\Delta Y/2$).

Low-Pass Filtering. Once a conditioned scatter estimate $ESR_1^{\ 2}(X,Y,\theta)$ for a projection has been generated, the data that it holds may be low-pass filtered (e.g., averaged) by any number of known ways to generate a third scatter estimate $ESR_1^{\ 3}(X,Y,\theta)$. For example, a moving two-dimensional averaging window (equal weighting) over the discrete X- and Y-coordinates similar to that used in formula [9] may be used to generate $ESR_1^3(X,Y,\theta)$ from $ESR_1^2(X,Y,\theta)$, the results of which can be equivalent to the following mathematical formula:

$$ESR_1^3(X, Y, \theta) = \frac{1}{N_X \cdot N_Y} \cdot \sum_{x=X-\frac{1}{2}\Delta X}^{X+\frac{1}{2}\Delta X} \sum_{y=Y-\frac{1}{2}\Delta Y}^{Y+\frac{1}{2}\Delta Y} ESR_1^2(x, y, \theta) \quad [12]$$

for each discrete X, each discrete $\theta$, and each discrete Y in the band from $(Y_{LL}-\Delta Y/2)$ to $(Y_{LL}+\Delta Y/2)$, where $N_Y$ is the number of pixels used in the summation of $ESR_1^2(x,y,\theta)$ over the Y-dimension, and where $N_X$ is the number of pixels used in the summation of $ESR_1^2(x,y,\theta)$ over the X-dimension. Typically, the value of $ESR_1^3(X,Y,\theta)$ is generated for only the Y-coordinate on the lateral line $(Y=Y_{LL})$, and in an exemplary embodiment, $N_Y$ may be approximately 10 pixels to 20 pixels (which span distance $\Delta Y$), and $N_X$ may also be approximately 10 pixels to 20 pixels (which span distance $\Delta X$). In one embodiment, $N_Y=N_X=15$. Instead of using an equal weighting of the pixel data, other weightings may be used, such as a two-dimensional Gaussian weighting. If $W(x-X,y-Y)$ represents a pixel-weighting function centered about the point (X,Y), then the following mathematical formula may be used:

$$ESR_1^3(X, Y, \theta) = \quad [13]$$
$$\frac{1}{N_X \cdot N_Y} \cdot \sum_{x=X-\frac{1}{2}\Delta X}^{X+\frac{1}{2}\Delta X} \sum_{y=Y-\frac{1}{2}\Delta Y}^{Y+\frac{1}{2}\Delta Y} W(x-X, y-Y) \cdot ESR_1^2(x, y, \theta)$$

where the double summation of the weighting function over the averaging area is equal to unity:

$$\sum_{x=X-\frac{1}{2}\Delta X}^{X+\frac{1}{2}\Delta X} \sum_{y=Y-\frac{1}{2}\Delta Y}^{Y+\frac{1}{2}\Delta Y} W(x-X, y-Y) = 1$$

Each value of $ESR_1^3(X,Y,\theta)$ generated in correspondence to formulas [12] and [13] comprises an average of a plurality of values of $ESR_1^2(x,y,\theta)$. In typical embodiments, formulas [12] and [13] need only be done for data points on the lateral line, meaning that $ESR_1^3(X,Y_{LL},\theta)$ need only be generated. In addition, the pixel values in each averaging window may be first examined to find the high and low values before computing the averages according to formulas [12] and [13], and the high and low values may thereafter be omitted from the average calculation.

Figure 4:
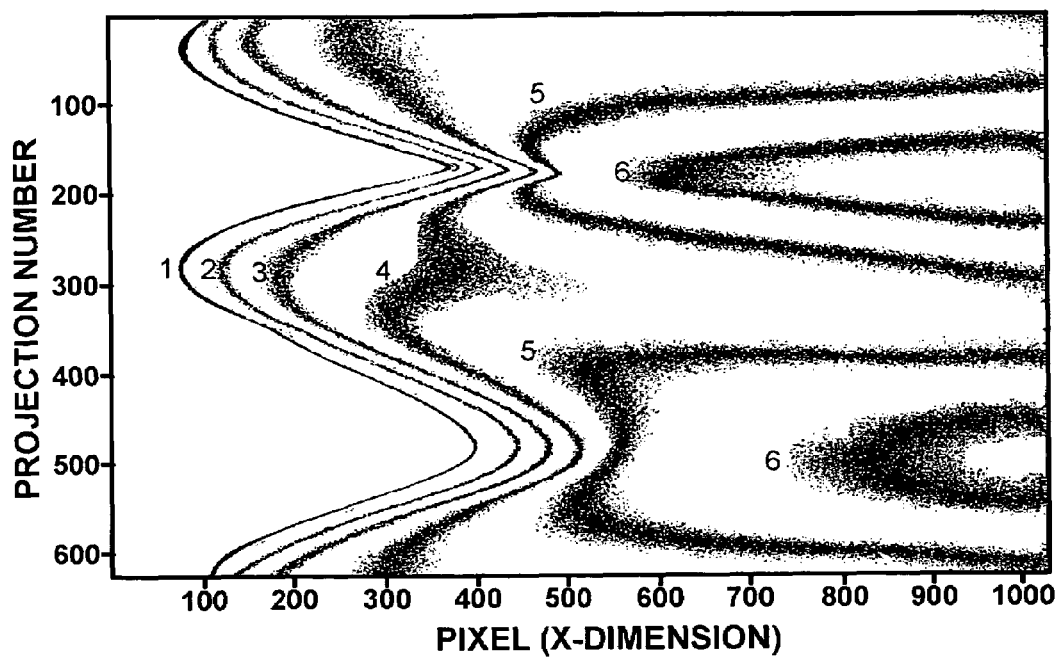
FIG. 4 is a graph of a scatter estimate in Sinogram form according to inventions of the present application.

The values of third scatter estimate $ESR_1^3(X,Y_{LL},\theta)$ at taken at $Y=Y_{LL}$ are shown as a function of X and $\theta$ in Sinogram form by FIG. 4. Six contour lines are shown and labeled in the figure (with line "1" being the highest value and line "6" being the lowest value), and the broad fuzzy quality of the contour lines is caused by the noise in the data. (The data presented in FIG. 4 was not truncated according to formula [11]; the truncation operation, when performed on the data shown in FIG. 4, removes the first two contour lines.) In this example, the first and second groups of projections were collected at the same angular displacement values $\theta$, and a total of approximately 620 projections were collected for each group. The scanned object is a portion of the pelvic region of a human model, with the model being offset so that only one edge of the object appears in each of the Sinogram rows. As previously indicated, the present inventions work for cases where the numbers of projections in the first and second groups are different. Typically, fewer projections are collected in the second group than in the first group, and the above scatter estimates are provided at fewer angular displacement values $\theta$ than the angular displacement values at which the first projection data $P_1(X,Y,\theta)$ was collected. In such cases, the third scatter estimate $ESR_1^3(X,Y_{LL},\theta)$ can have missing estimated values at particular angular displacement values $\theta$. Interpolation of the scatter estimates with respect to angular displacement using any known interpolation method can be done to provide values for any missing estimated values. The data provided by the Sinogram of FIG. 4, whether or not interpolation is used, can be represented as a fourth scatter estimate $ESR_1^4(X,\theta)$, which is not a function of Y.

Next, the data in the fourth scatter estimate $ESR_1^4(X,\theta)$ is low-pass filtered by any number of known ways to provide a fifth scatter estimate $ESR_1^5(X,\theta)$ that has reduced noise. As one example, a moving two-dimensional averaging window (equal weighting) over the discrete X-coordinates and $\theta$ values, similar to that used in formula [9], may be used to generate $ESR_1^5(X,\theta)$, the results of which can be equivalent to the following mathematical formula:

$$ESR_1^5(X, \theta) = \frac{1}{N_X \cdot N_\theta} \cdot \sum_{x=X-\frac{1}{2}\Delta X}^{X+\frac{1}{2}\Delta X} \sum_{\varphi=\theta-\frac{1}{2}\Delta\theta}^{\theta+\frac{1}{2}\Delta\theta} ESR_1^4(x, \varphi) \quad [14]$$

for each discrete value of X and each discrete value of $\theta$, where $N_\theta$ is the number of pixels used in the summation of $ESR_1^4(X,\theta)$ over the $\theta$-dimension, and where $N_X$ is the number of pixels used in the summation of $ESR_1^4(x,\theta)$ over the X-dimension. Typically, No may range from 40 pixels to 60 pixels (which span distance $\Delta\theta$), and $N_X$ may also range from 40 pixels to 60 pixels (which span distance $\Delta X$). In an exemplary embodiment, each of $N_\theta$ and $N_X$ is equal to 50. Instead of using an equal weighting of the pixel data, other weightings may be used, such as a two-dimensional Gaussian weighting. If $W(x-X,\phi-\theta)$ represents a pixel-weighting function centered about the point $(X,\theta)$, then the following mathematical formula may be used:

$$ESR_1^5(X, \theta) = \sum_{x=X-\frac{1}{2}\Delta X}^{X+\frac{1}{2}\Delta X} \sum_{\varphi=\theta-\frac{1}{2}\Delta\theta}^{\theta+\frac{1}{2}\Delta\theta} W(x-X, \varphi-\theta) \cdot ESR_1^4(x, \varphi) \quad [15]$$

for each discrete value of X and each discrete value of $\theta$, where the double summation of the weighting function over the averaging area is equal to unity:

$$\sum_{x=X-\frac{1}{2}\Delta X}^{X+\frac{1}{2}\Delta X} \sum_{\varphi=\theta-\frac{1}{2}\Delta\theta}^{\theta+\frac{1}{2}\Delta\theta} W(x-X, \varphi-\theta) = 1.$$

Figure 5:
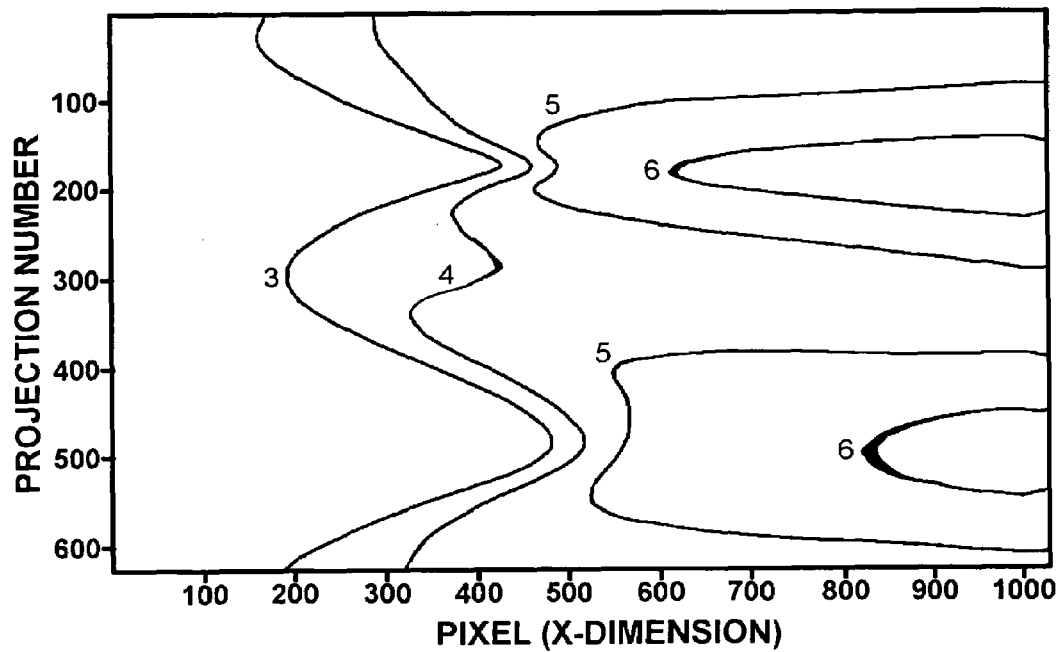
FIG. 5 is a graph of another scatter estimate in Sinogram form according to inventions of the present application.

Each value of $ESR_1^5(X,\theta)$ generated in correspondence to formulas [14] and [15] comprises an average of a plurality of values of $ESR_1^4(x,\phi)$. The pixel values in each averaging window may be first examined to find the high and low values before computing the averages according to formulas [14] and [15], and the high and low values may thereafter be omitted from the average calculation. The values of an exemplary fifth scatter estimate $ESR_1^5(X,\theta)$ are shown as a function of X and $\theta$ in Sinogram form by FIG. 5. The values of this exemplary fifth scatter estimate are generated from the data shown in FIG. 4 using formula [14] with both of $N_\theta$ and $N_X$ set to 50 pixels. Four contour lines are shown and labeled in FIG. 5 (with line "3" being the highest value and line "6" being the lowest value), where the first two lines have been removed by a truncation process. The contour lines in FIG. 5 are sharper than those in FIG. 4, which is due to the reduction of the noise caused by the spatial filtering.

In both of formulas [14] and [15], the X dimension of the averaging window can be decreased for values of X less than $N_X/2$ and values of X greater than $(X_{MAX}-N_X/2)$ to account for the fact that there is no data for values of X less than 1 or greater than $X_{MAX}$. The averaging window in the $\theta$ dimension does not need to be reduced since the Sinogram is a loop upon itself in this dimension. That is to say, when the averaging window starts from $\phi=1$, values of $ESR_1^4(x,\phi)$ from $\phi=(\theta_{MAX}-N_\theta/2)$ through $\theta_{MAX}$ can be used for values of $ESR_1^4(x,\phi)$ from $(\phi=N_\theta/2$ through $(\phi=0$; and when the summation window approaches $\theta_{MAX}$, values of $ESR_1^4(x,\phi)$ from $(\phi=1$ through $N_\theta/2$ can be used for values of $ESR_1^4(x,\phi)$ from $(\phi=(\phi_{MAX}+1)$ through $(\theta_{MAX}+N_\theta/2)$.

Figure 6:
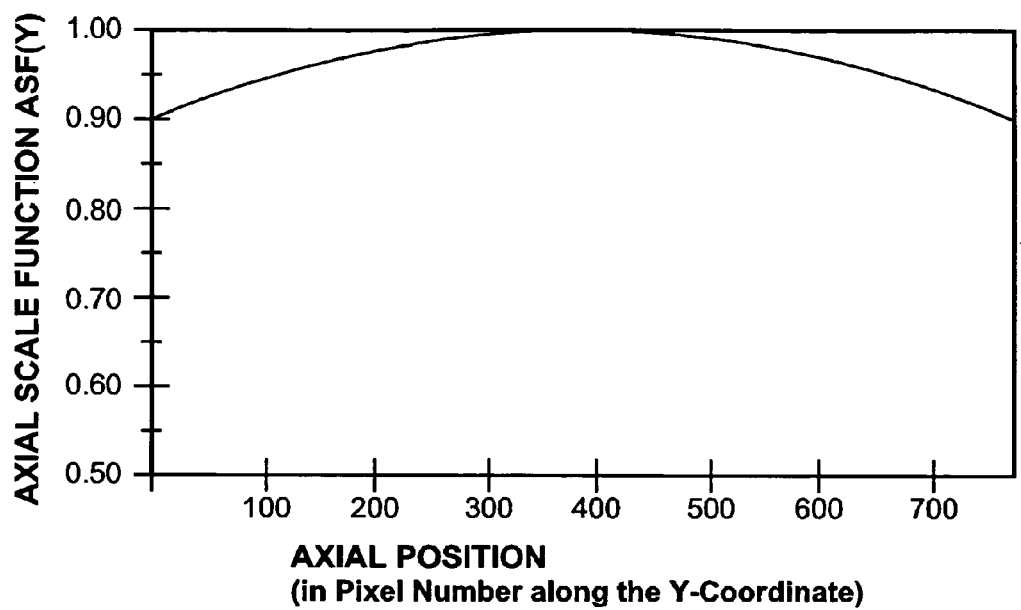
FIG. 6 is a graph of an exemplary axial scale factor according to inventions of the present application.

Extension of Estimates to All Discrete Y-coordinates. The fifth scatter estimate $ESR_1^5(X,\theta)$ provides an estimate of the scattered radiation along the lateral line $(Y=Y_{LL})$ for each of the angular displacement values $\theta$ used in the first group of projections, but does not directly provide an estimate for other lines parallel to the lateral line (i.e., for other values of Y). The inventors have found that the scattered radiation along other lines parallel to the lateral line substantially follows the same shape as the radiation along the lateral line, but is scaled by a factor less than unity. The scale factor for a particular line, which is called herein the axial scale factor ASF(Y), decreases with the separation distance between the particular line and the lateral line, with the decrease generally having a parabolic form. For example, parallel lines adjacent to the lateral line have an axial scale factor substantially equal to unity, whereas parallel lines at the extremes (Y=1 and $Y=Y_{MAX}$) have axial scale factors of approximately 0.9, and parallel lines at middle points $(Y=0.25 \cdot Y_{MAX}$ and $Y=0.75 \cdot Y_{MAX})$ have axial scale factors of approximately 0.975. An exemplary form of the axial scale factor ASF(Y) is shown in FIG. 6, and can be approximated by the formula:

$$ASF(Y) \approx 1 - 0.4 \cdot \left(\frac{Y-Y_{LL}}{2Y_{LL}}\right)^2 \quad [16]$$

Using the axial scale factor ASF(Y), a sixth scatter estimate, which is a function of Y as well as X, may be generated according the following formula:

$$ESR_1^6(X,Y,\theta)=ESR_1^5(X,\theta)\cdot ASF(Y). \quad [17]$$

Estimate $ESR_1^6(X,Y,\theta)$ is suitable for generating corrected projections, as discussed next.

Generation and Use of Corrected Projections. A set of corrected projection data $CP_1(X,Y,\theta)$ may be generated from the first group of projections $P_1(X,Y,\theta)$ and the sixth scatter estimate $ESR_1^6(X,Y,\theta)$ according to the formula:

$$CP_1(X,Y,\theta)=P_1(X,Y,\theta)-ESR_1^6(X,Y,\theta) \quad [18]$$

Figure 10:
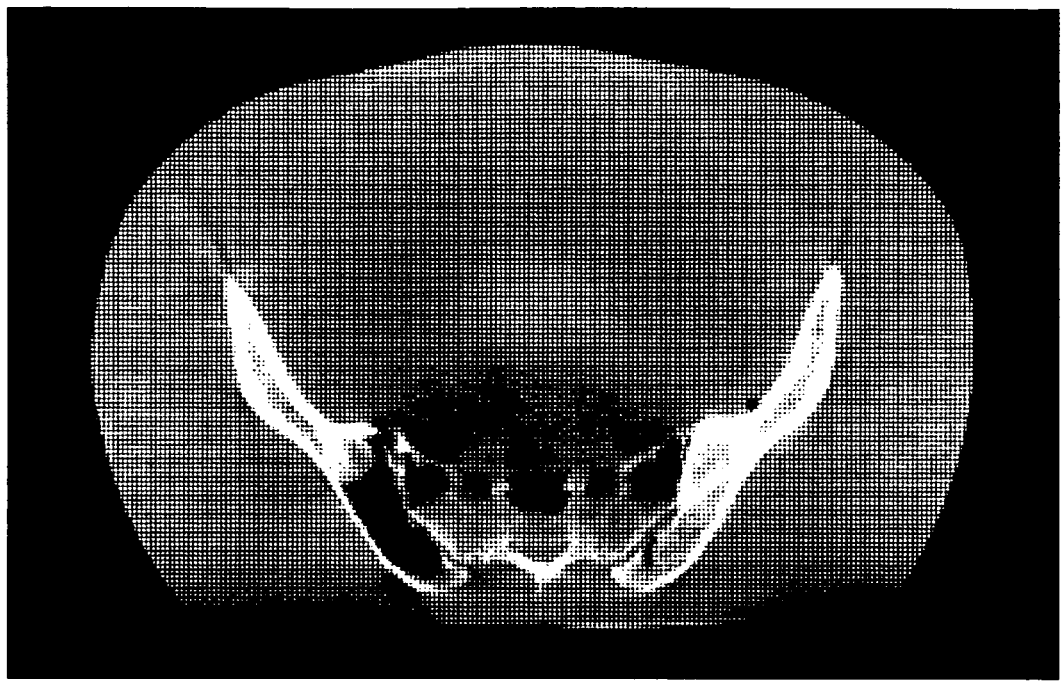
FIG. 10 shows a cross-section of a calibrated phantom of a human pelvis without correction for scattering according to the prior art.
Figure 11:
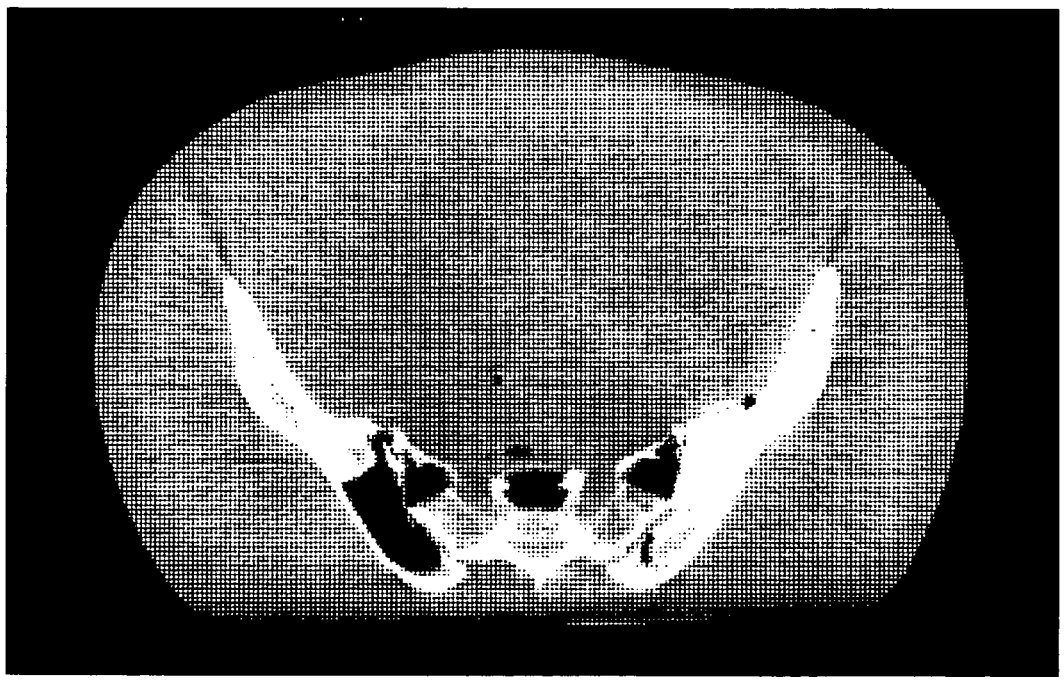
FIG. 11 shows the same cross-section as FIG. 10 after correction for the scattering according to inventions of the present application.

The corrected projections may then be used in any image reconstruction method, such as the Feldkamp method, to enable the production of CT slices of the object. FIG. 10 shows a cross-section of a calibrated phantom of a human pelvis without correction for scattering, and FIG. 11 shows the same cross-section after correction for the scattering according to the inventions. The overall darkness and non-uniform tone of the image in FIG. 10 indicates an overall lowering of the CT numbers from their true values for the image, whereas the overall uniformly lighter tone of the image in FIG. 11 indicates that the CT numbers for the image are closer to the correct values. Also, as artifacts, the image of FIG. 10 has a broad, subtle white dot in the center of the image, and a larger, subtle white annular ring surrounding the white dot. These artifacts are reduced in the image of FIG. 11.

Extensions and Further Embodiments of the Inventions. In the case where the second group of projections is collected first, each of the scatter estimates $ESR_1^1(X,Y,\theta)$ through $ESR_1^6(X,Y,\theta)$ may be generated as the data needed for them becomes available. For example, a software processing thread may be initiated for the generation of each of the estimates, with each generating a result as its input data becomes available, and thereafter outputting results for other of the threads to use. Likewise, the generation of the corrected projections $CP_1(X,Y,\theta)$ may be generated as $P_1(X,Y,\theta)$ and $ESR_1^6(X,Y,\theta)$ become available, and an image reconstruction method may be initiated as soon as corrected projections become available. Software processing threads may be initiated for the generation of $CP_1(X,Y,\theta)$ and the reconstruction method.

In the above description, the scatter multiplier $M_A(F_W)$ was introduced early in the process at formula [8B]. Since it is a scalar quantity, it may be appreciated by one of ordinary skill in the art that $M_A(F_W)$ can be introduced later in the generation process of the estimates, such as at any of formulas [11]-[15] and [17], or the generation of $ESR_1^4(X,\theta)$ (the Sinogram form). In the above exemplary description, each of the scatter estimates was based on a difference between projections in the first and second groups having the same angular displacement value (e.g., $P_1(X,Y,\theta i)-P_2(X,Y,\theta i,F_W)$). As indicated in the above section on data collection, some of the projections of the first group may be missing, but each missing projection may be replaced by a pseudo-projection that is generated by projections having angular displacement values close to that of the missing projection. Further in this regard, it may be appreciated that if some or all of the angular displacement values used in the second group do not match respective ones in the first group, the data of the projection in one or both of the groups can be interpolated to common angular displacement values, where the common values may be the same as, or different from, the angular displacement values used in one or both of the groups. The data taken from a group of projections and used to generate an estimate for a particular angular displacement value is referred to herein (and in the claims) as a representation of the radiographic projection data for that particular angular displacement value taken with the fan blades set at a corresponding distance.

Accordingly, the inventive estimation process of the present application may be broadly described as follows. A first group of radiographic projections taken by the two-dimensional imaging device at a corresponding first plurality of angular displacement values is obtained, with the projections of the first group being taken with radiation from the source incident upon a first band of pixels of the imaging device. A second group of radiographic projections taken by the two-dimensional imaging device at a corresponding second plurality of angular displacement values is obtained, with the projections of the second group being taken with radiation from the source incident upon a second band of pixels of the imaging device. The second band is narrower than the first band, and preferably disposed within the first band. The projections can be obtained by receiving the projection data as inputs to the estimation process or by using imaging system 100 or 100' to generate the projection data. The groups may be obtained in any order or in overlapping fashion. Thereafter, estimates of the scattered radiation within at least a portion of the second band of pixels is generated for a third plurality of angular displacement values, where the third plurality of angular displacement values may have common values or different values from those of the first and second groups. Each estimate comprises a difference between a first representation of the radiographic projection data for an angular displacement value of the third plurality with radiation from the source incident upon a first band of pixels of the imaging device and a second representation of the radiographic projection data for the same angular displacement value with radiation from the source incident upon a second, narrower, band of pixels, with the first representation being generated from the at least one radiographic projection of the first group and the second representation being generated from at least one radiographic projection of the second group. This broadly encompasses the process of generating an estimate as $\{P_1(X,Y,\theta) - P_2(X,Y,\theta,F_W)\}$, which is useful for small values of $F_W$ even though the estimate does not comprise $M_A(F_W)$.

Figure 7:
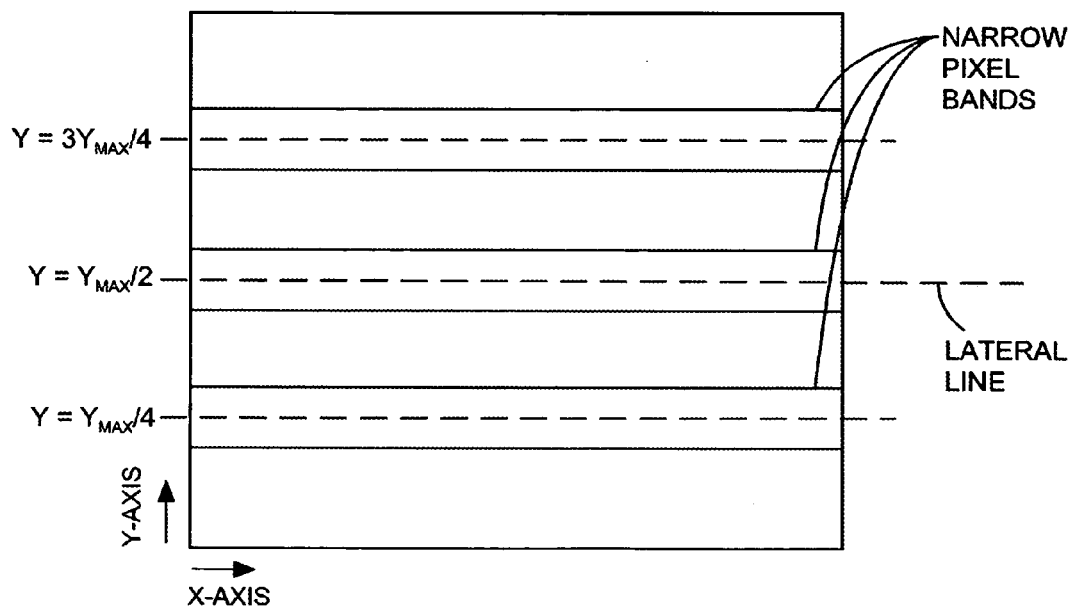
FIG. 7 is a top plan view of the pixels of an exemplary two-dimensional imaging device showing the use of three narrow pixel bands which may be used to generate scatter estimates along three corresponding lines according to inventions of the present application.

In the above examples, the scattered radiation was estimated along the lateral line ($Y=Y_{LL}$) centered on the Y-dimension of the imaging device, and thereafter extended to Y-coordinates of the imaging device. The lateral line need not be centered on the Y-dimension of the imaging device, and can have other locations on the two-dimensional imaging device. In addition, the scattered radiation may be estimated along two or more lines (e.g., $Y=Y_{MAX}/2$, $Y=Y_{MAX}/4$ and/or $Y=3Y_{MAX}/4$) so as to obtain an empirical measurement of the curvature of the axial scale factor function ASF(Y). For this, the fan blade can be modified to enable a narrow band to be created along each such line when the second projections are obtained. An exemplary modification incorporates an interior slot in one or both of the fan blades. FIG. 7 illustrates the case where the scattered radiation is estimated along three lines $Y=Y_1$, $Y_2$, and $Y_3$ with three corresponding narrow bands for the second projections. A set of estimates $ESR_1^N(X,Y,\theta)$ N=1,2, . . . 5 may then be generated from each of the narrow bands by the processes described above, resulting in three instances of fifth estimates $ESR_1^{5,Y1}(X,\theta)$, $ESR_1^{5,Y2}(X,\theta)$, and $ESR_1^{5,Y3}(X,\theta)$, where the superscripts Y1, Y2, and Y3 have been added to distinguish the three instances. With the additional estimates, a separate axial scale factor function $ASF_{xi,\theta j}(Y)$ can be generated for each group of pixel data having the same discrete X-coordinate Xi and the same angular displacement value $\theta j$ by curve-fitting a parabolic function or similar form to the three corresponding values of $ESR_1^{5,Y1}(Xi,\theta j)$, $ESR_1^{5,Y2}(Xi,\theta j)$, and $ESR_1^{5,Y3}(Xi,\theta j)$, and by using the set of functions $ASF_{Xi,\theta j}(Y)$ in formula [17] in place of ASF(Y). In addition, a generalized function $ASF_{\theta j}(X,Y)$ having fitting parameters may be proposed for each angular displacement value $\theta j$ and curve-fitted to three sets of estimates $ESR_1^{5,Y1}(X,\theta j)$, $ESR_1^{5,Y2}(X,\theta j)$, and $ESR_1^{5,Y3}(X,\theta j)$. Such a generalized function may comprise a polynomial form having terms in both X and Y, and cross terms in XY. As an extension of this approach, the three sets of estimates may be provided as inputs to any curve-fitting function to directly provide $ESR_1^6(X,Y,\theta)$ without directly generating the axial scale factor functions. Such an approach is particularly attractive when four or more sets of the fifth estimates are available, since high-order spline curve-fitting functions and similar functions may be used. This approach may be generally represented by the following formula, which can be used in place of formula [17]:

$$ESR_1^6(X,Y,\theta) = \text{Curve\_Fitting\_Functions}(ESR_1^{5,Y1}(X,\theta j),$$

$$ESR_1^{5,Y2}(X,\theta j),$$

$$ESR_1^{5,Y3}(X,\theta j), \ldots ) \quad [19]$$

As a further modification based on the above approaches, a single fan-blade gap can be used, with the gap being moved from one line ($Y_1$) to the next ($Y_2$), and to the next ($Y_3$), and so on, at successive intervals of projections. For example, the gap may be located at line $Y_1$ at one projection, moved during the next three projections to be at line $Y_2$ by the fifth projection, thereafter moved during the next three projections to be at line $Y_3$ by the ninth projection, returned back to line $Y_1$ by the thirteenth projection, and so on. This gives the fan-blade drive a period of time (e.g., the time span by three projections) to move to the next line in the sequence. At each line, the appropriate fifth scatter estimate is generated according to the methods described above for the following projections:

$$ESR_1^{5,Y1}(Xi,\theta_k), \text{ for } k=1,13,25,37,$$

$$ESR_1^{5,Y2}(Xi,\theta_{k+4}), \text{ for } k=1,13,25,37,$$

$$ESR_1^{5,Y3}(Xi,\theta_{k+8}), \text{ for } k=1,13,25,37,$$

Each series of fifth estimates is missing values at eleven of every twelve projections, but interpolation may be used to generate the missing value. For example, $ESR_1^{5,Y1}(Xi,\theta_1)$ and $ESR_1^{5,Y1}(Xi,\theta_{13})$ may be used to generate interpolated values for $ESR_1^{5,Y1}(Xi,\theta k)$ k=2,3, . . . 12. By generating interpolated fifth estimates for the missing projections of each line, a set of axial scale factor functions $ASF_{xi,\theta j}(Y)$ may be generated for every projection as described above, or the curve-fitting function of formula [19] may be applied. In addition, since the scattered radiation is a slowly changing function, less extensive interpolation may be used. For example, a set of axial scale factor functions $ASF_{xi,\theta j}(Y)$ or a set of curve-fitted formulas [19] may be generated for each projection for which measured values for $ESR_1^{5,Y2}(Xi,\theta_{k+4})$ are available (k=1, 13, 25, 37, . . . ), and the set of axial scale functions or curve-fitting functions of formula [19] may be reused for the previous five or six projections and for the five or six succeeding projections. For curve fitting the data to generate the axial scale factor functions $ASF_{xi,\theta j}(Y)$ or the functions of formula [19], the data needed at lines $Y_1$ and $Y_3$ may be generated by interpolation from adjacent projections for which measured data is available for these lines. While these embodiments have been illustrated with the use of three Y-lines, it may be appreciated that more Y-lines may be used, such as ten or more. Additional Y-lines would enable higher order curve-fitting procedures to be used (such as well-known spline-fitting procedures). With a higher number of Y-lines, the fan blades may be moved within the time duration of one or two projections. In addition, the fan blades may be implemented by one or more moving plates, each plate having a slit parallel to the lateral line ($Y_{LL}$) to provide the fan blades. A planetary gear system may be used to convey the moving plates. The one or more moving plates readily facilitate a continuous motion for the fan-blade gap where a Y-line of data may be collected at each projection. The one or more moving plates may be retracted away from the projection line when the first group of projections is collected.

While the above examples have estimated the scattered radiation along one or more lateral lines that are parallel to the Y-axis, it may be appreciated that the estimates can be generated along one or more transverse lines that are parallel to the X-axis. The fan blades and the fan blade drive can readily be rotated 90 degrees to provide narrow bands that run along the one or more transverse lines.

In some applications of the present inventions, a patient may undergo periodic scans at different times, usually on different visits to the scanning facility. Instead of collecting the second group of projections $P_2(X,Y,\theta,F_W)$ each time the patient is scanned, the second group of projections $P_2(X,Y,\theta,F_W)$ may be collected on the first visit and thereafter reused for subsequent visits. In each visit, the portion of the patient's body being scanned may be aligned to alignment markers on the patient support table in a noted manner so that the second group of projections is substantially aligned to the subsequent first groups of projections collected during subsequent visits. As another approach, the sixth scatter estimate $ESR_1^6(X,Y,\theta)$ may be generated at the patient's first visit, and reused during subsequent visits. In this case as well, the portion of the patient's body being scanned may be aligned to alignment markers on the patient support table in a noted manner. Instead of aligning the patient to markers on the support table, or in addition thereto, one or more projections $P_1(X,Y,\theta)$ from the first visit may be collected and compared to corresponding projections of subsequent visits to determine the patient's relative position during each subsequent visit. From the comparison, offsets in the X and Y axes can be computed which can be used to mathematically align the correction data (e.g., $P_2(X,Y,\theta,F_W)$ or $ESR_1^6(X,Y,\theta)$) from the first visit to the projections collected during subsequent visits, or vice versa. The width of the first bands used in the initial visit and subsequent visit need be identical in size and extent, but are preferably close to one another (and closer to one another in width than to the second band). In addition, if the scanning parameters are different between the first visit and a subsequent visit, the correction data (e.g., $P_2(X,Y,\theta,F_W)$ or $ESR_1^6(X,Y,\theta)$) can be scaled to account for such differences. Of the scanning parameters, the radiation intensity is most likely to be different. So, for example, if the source current (which is generally proportional to emitted radiation intensity), is 2 mA during the first visit and 2.5 mA during the subsequent visit, then the correction data (e.g., $P_2(X,Y,\theta,F_W)$ or $ESR_1^6(X,Y,\theta)$) would be scaled by a factor of (2.5 mA/2 mA)=1.25.

The present inventions may be practiced in the case where a bowtie filter is disposed near the radiation source to provide spatial shaping to the emitted radiation intensity. The spatial variation caused by the bowtie filter equally affects both groups of projections, and the effects of the bowtie filter are cancelled out.

Figure 2B:
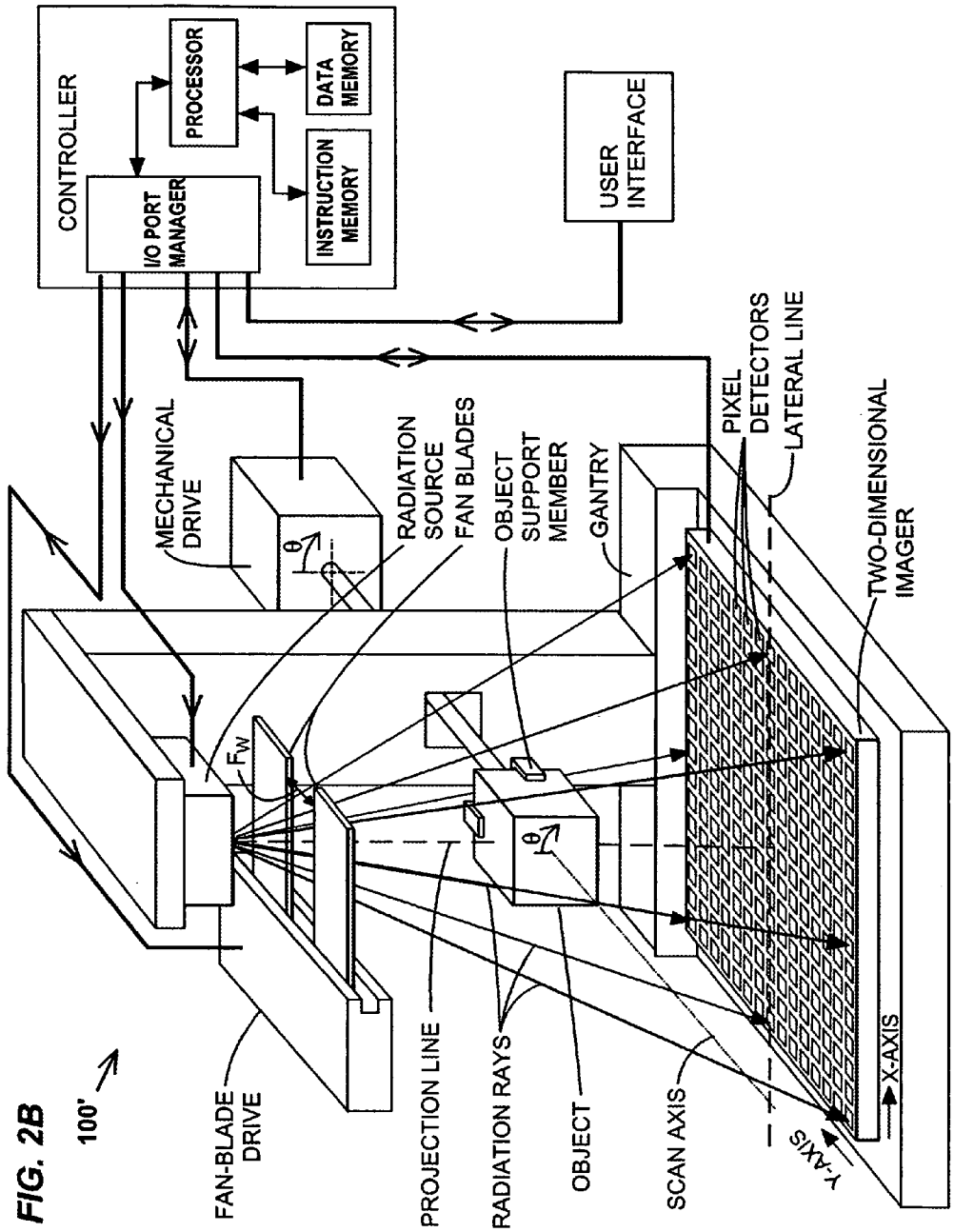
FIG. 2B is a schematic diagram of a second exemplary embodiment of a radiation imaging system according to the present invention.

Exemplary Instruction Sets. Having described exemplary imaging systems and methods of generating estimates of the scattered radiation, exemplary instruction sets for directing a processor, such as that of the controller in FIGS. 2A and 2B, are now described. Each of the instruction sets is embodied on a computer readable memory, and can be loaded from there into the instruction memory of the controller shown in FIGS. 2A and 2B. The instruction memory is itself an exemplary form of a computer readable memory.

A first exemplary computer program product is illustrated in FIG. 8, and it comprises instruction sets #1-#8, #9A, #9B, and #9C embodied on a computer readable medium that directs a processor to perform respective tasks. The processor may be associated with an imaging system (such as the processor shown in FIGS. 2A and 2B), or may be a standalone processor which receives projection data and related information from another computer readable medium. The instruction sets shown in FIG. 8 implement the above-described methods that relate to projections of the second group which have one or more second bands that are at the same position(s) for each of the projections in the second group. The instruction sets may be executed one after another in sequential order, or may be executed in an overlapping manner as separate processes on respective process threads. In the latter case, the instruction sets may comprise data structures that facilitate inter-process communication between the instruction sets so that each instruction set can notify the next instruction set in the sequence that its output data is ready to be received as input data for processing. Such data structures are well-known to the art and a description thereof is not needed for one of ordinary skill in the art to construct and use the instruction sets described herein.

Instruction Set #1 directs the data processor to obtain a first group of radiographic projections taken by the two-dimensional imaging device at a corresponding first plurality of angular displacement values, with the projections of the first group being taken with radiation from the source incident upon a first band of pixels of the imaging device, as described above. Instruction Set #1 can comprise a first subset of instructions (e.g., subroutine) that direct the processor to read the projections from an electronic file, or a second subset of instructions that direct the processor to run imaging system 100 and/or 100' to collect the projections, or both first and second subsets of instructions. In the latter case, the first set of instructions can have instructions that direct the processor to present a dialog box or window to a human user of the program that enables the user to select how the first group of projections is obtained (i.e., which of the subsets of instructions to use), and each of the subsets of instructions can have instructions that direct the processor to present a dialog box or window to a human user of the program to enable the user to input parameters on where or how the projections will be obtained.

In a similar manner, Instruction Set #2 directs the data processor to obtain a second group of radiographic projections taken by the two-dimensional imaging device at a corresponding second plurality of angular displacement values as described above, with the projections of the second group being taken with the radiation from the source incident upon at least one second band of pixels of the imaging device, and with each second band being narrower than the first band. Instruction Set #2 can comprise a first subset of instructions (e.g., subroutine) that direct the processor to read the projections from an electronic file, or a second subset of instructions that direct the processor to run imaging system 100 and/or 100' to collect the projections, or both first and second subsets of instructions. In the latter case, the second set of instructions can have instructions that direct the processor to present a dialog box or window to a human user of the program that enables the user to select how the second group of projections is obtained, and each of the subsets of instructions can have instructions that direct the processor to present a dialog box or window to a human user of the program to enable the user to input parameters on where or how the projections will be obtained. Instruction Set #2 further comprises instructions that direct the processor to obtain an indication of the number and location of second bands within each radiographic projection of the second group and/or that direct the processor to scan (i.e., analyze) each projection of the second group to determine the number and location of the second bands. In the case of the exemplary computer program product uses system 100 or 110' to obtain the projections, a dialog box may be used to enable the user to specify the locations of the second bands, or a default location specification may be used. In the latter case, the default may be set by hardware, and Instruction Set #2 directs the processor to scan the projections to find the number and location of the second bands. In a case in which the first and second groups of projections are collected by an imaging system during a single scan, portions of Instruction Sets #1 and #2 relating to the collection of the projections can be merged together in a subroutine that is run after the above-described dialog boxes/windows have been presented to the user.

Instruction Set #3 directs the data processor to generate a first set of estimates of the scattered radiation (e.g., $ESR_1^1(X,Y,\theta)$) within at least a portion of each second band of pixels for a third plurality of angular displacement values, with each estimate of the first set being for a particular angular displacement value of the third plurality and for a particular second band. Each estimate comprises a difference between a first representation of the radiographic projection data taken with the source radiation incident upon the first band of pixels and a second representation of the radiographic projection data taken with the source radiation incident upon the particular second band of pixels, as described above. These instructions may use formula [8B] described above.

Instruction Set #4 directs the data processor to generate a second set of estimates of the scattered radiation (e.g., $ESR_1^2(X,Y,\theta)$) within at least a portion of each second band of pixels for the third plurality of angular displacement values. Each estimate of the second set comprises a respective estimate of the first set when the respective estimate of the first set is below a truncated value, and each estimate of the second set comprises the truncated value when the respective estimate of the first set is above the truncated value. An estimate of the second group and its respective estimate of the first group are for the same pixel location and for the same angular displacement value. Instruction Set #4 may use a preset truncated value, or may generate it from the first set of estimates by the exemplary process outlined above and illustrated by formulas [9] and [10]. The execution of Instruction Set #4 is optional, but currently preferred. If the Instruction Set #4 is not used, Instruction Set #5 may work from the first set of estimates instead of the second set of estimates.

Instruction Set #5 directs the data processor to generate a third set of estimates of the scattered radiation (e.g., $ESR_1^3(X,Y,\theta)$) for a row of pixels within each second band of pixels for the third plurality of angular displacement values, with each such estimate comprising a spatial average of a plurality of estimates of the second set for a particular angular displacement value particular second band. Instruction Set #5 can use formulas [12] or [13] described above. The estimates for the row of pixels for a particular angular displacement value and second band are collectively called a "row estimate" for the particular angular displacement value and second band.

Instruction Set #6 directs the data processor to assemble, for each second band of pixels, the row estimates of each associated third set of estimates into a respective array (e.g., Sinogram) of a spatial dimension of the two-dimensional imager versus angular displacement values. Each assembled array (e.g., Sinogram) being a respective fourth set of estimates of the scattered radiation (e.g., $ESR_1^4(X,\theta)$) for the respective second band of pixels. The spatial dimension of the assembled arrays can be either of the two dimensions of the two-dimensional imaging device. In the prior descriptions, the X-dimension was used to illustrate the inventions.

Instruction Set #7 directs the data processor to generate, for each second band of pixels, a respective fifth set of estimates of the scattered radiation (e.g., $ESR_1^5(X,\theta)$) in an array form (e.g., Sinogram) of the spatial dimension versus angular displacement values. The spatial dimension is the same spatial dimension used to assemble the fourth set of estimates. Each fifth set of estimates is generated from the respective fourth set of estimates that was assembled for the same second band of pixels. Each estimate of the fifth set is for a pixel in the spatial dimension and an angular displacement value, and comprises an average of a plurality of estimates of a respective fourth set that span a plurality of pixels in the spatial dimension and a plurality of pixels in the dimension for angular displacement values. In this regard, Instruction Set #7 can use formulas [14] or [15] described above.

Instruction Set #8 directs the data processor to obtain an indication of the form in which to generate a sixth set of estimates of the scattered radiation. The indication may be provided by a human user, read from a data file (such as a file providing the projection data), or set to a default indication. Each estimate of the sixth set is for all the pixels of the imaging device (in both dimensions) at a particular angular displacement value, and is generated from one or more fifth sets of estimates according to a number of forms depending on the functionality of the axial scale factor. If the sixth set of estimates is to be generated using a preset axial scale factor ASF(Y), which is called herein the "first form," then Instruction Set #8 will execute Instruction Set #9A (Instruction Sets #9B and #9C are not executed). If the sixth set of estimates is to be generated using a set of curve-fitted axial scale factor functions $ASF_{xi,\theta j}(Y)$ or a generalized axial scale factor function $ASF^{\Theta j}(X,Y)$, which is called herein the "second form," then Instruction Set #8 will execute Instruction Set #9B (Instruction Sets #9A and #9C are not executed). The second form requires that there be at least two second bands of pixels for the projections of the second group. Finally, if the sixth set of estimates is to be generated according to a curve-fitting function from the fifth set of estimates using formula [19], which is called herein the "third form," then Instruction Set #8 will execute Instruction Set #9C (Instruction Sets #9A and #9B are not executed). The third form requires that there be at least two second bands of pixels for the projections of the second group, and preferably three or more second bands. A first portion of Instruction Set #8 can be executed before Instruction Set #3 is executed in order to get the indication of which form to use. The remaining portion of Instruction Set #8 can be executed after the execution of Instruction Set #3 has begun in order to start the execution of one of Instruction Sets #9A, #9B, and #9C, which are described below.

Instruction Set #9A directs the data processor to generate the sixth set of estimates of the scattered radiation (e.g., $ESR_1^6(X,Y,\theta)$) for both dimensions of the imaging device and for the third plurality of angular displacement values. Each estimate of the sixth set is for the pixels of the imaging device at a particular angular displacement value, and each comprises a row of the fifth set of estimates in the spatial dimension for the particular angular displacement value multiplied by a scale function, the scale function being a preset function in the second dimension of the imaging device. In this regard, Instruction Set #9A can use formula [17] described above.

Instruction Set #9B directs the data processor to generate the sixth set of estimates of the scattered radiation (e.g., $ESR_1^6(X,Y,\theta)$) for both dimensions of the imaging device and for the third plurality of angular displacement values. Each estimate of the sixth set is for the pixels of the imaging device at a particular angular displacement value, and each comprises a row of the fifth set of estimates in the spatial dimension for the particular angular displacement value multiplied by a scale function, each scale function being a function in the second dimension of the imaging device. Instruction Set #9B further comprises a subset of instructions that directs the data processor to generate each scale function from the fifth sets of estimates, as described above. A scale function may be generated for each group of pixels having the same coordinate in the first dimension of the two-dimensional imager (e.g., same discrete X-coordinate) and the same angular displacement value, or a single generalized function $ASF_{\theta_j}(X,Y)$ may be generated for use by all of the pixels having the same angular displacement value.

Instruction Set #9C directs the data processor to generate the sixth set of estimates of the scattered radiation (e.g., $ESR_1^6(X,Y,\theta)$) for both dimensions of the imaging device and for the third plurality of angular displacement values. Each estimate of the sixth set is for the pixels of the imaging device at a particular angular displacement value, and is generated from at least one curve-fitting function that has the fifth sets of estimates at the particular angular displacement value as inputs. In this regard, Instruction Set #9C can use formula [19] described above.

The instruction sets shown in FIG. 8 are for cases where the projections of the second group have one or more second bands, each such band being in the same position for each of the projections in the second group. As indicated above, a single second band may be used, but its location may be moved among a plurality of line locations as the projections of the second group are taken. Thus, each instance of the second band in the projection data has a location that varies among a plurality of line locations depending upon the projection number, and thus it depends upon the angular displacement value for the projection. An exemplary computer program product for this situation can be the same as the computer program product illustrated in FIG. 8, but with Instruction Sets #5, #6, and #7 replaced by Instruction Sets #5A, #6A, and #7A, respectively. The replacement instruction sets are illustrated in FIG. 9 and described in greater detail below.

Instruction Set #5A directs the data processor to generate a third set of estimates of the scattered radiation for a row of pixels within each instance of the second band of pixels for the third plurality of angular displacement values. Each estimate of the third set comprises a spatial average of a plurality of estimates of the second set for a particular angular displacement value and particular instance of the second band. Instruction Set #5A can use formulas [12] or [13] described above. The estimates of the third set for the row of pixels provide a row estimate for an angular displacement value and a particular instance of the second band, with the row estimate being associated with the line location of the particular instance of the second band from which it is generated.

Instruction Set #6A directs the data processor to assemble the row estimates associated with the same line location into a respective array (e.g., Sinogram) of a spatial dimension versus angular displacement values. Each assembled array is a respective fourth set of estimates of the scattered radiation for the respective line location. The spatial dimension of the array of each fourth set of estimates corresponds to a first dimension of the two-dimensional imaging device. Each fourth set of estimates of the scattered radiation for a respective line location has missing estimated values at a plurality of angular displacement values because of the moving nature of the second band, and so a preferred embodiment of Instruction Set #6A further comprises instructions that direct the processor to generate the missing estimates by interpolation of estimates at a plurality of other angular displacement values. Any known interpolation method may be used.

Finally, Instruction Set #7A directs the data processor to generate, for each line location, a respective fifth set of estimates of the scattered radiation in an array form of the spatial dimension versus angular displacement values. Each fifth set of estimates is generated from the respective fourth set of estimates that was assembled for the same line location. Each estimate of the fifth set is for a pixel in the spatial dimension and an angular displacement value, and comprises an average of a plurality of estimates of a respective fourth set that span a plurality of pixels in the spatial dimension and a plurality of pixels in the dimension for angular displacement values. For such estimates, Instruction Set #7A can use formulas [14] or [15] described above.

While the present inventions have been particularly described with respect to the illustrated embodiments, it will be appreciated that various alterations, modifications and adaptations may be made based on the present disclosure, and are intended to be within the scope of the present inventions. While the inventions have been described in connection with what are presently considered to be the most practical and preferred embodiments, it is to be understood that the present inventions are not limited to the disclosed embodiments but, on the contrary, are intended to cover various modifications and equivalent arrangements included within the scope of the appended claims.

What is claimed is:

1. A method of estimating scattered radiation in radiographic projections of an object, the radiographic projections generated by a radiation source, a two-dimensional imaging device adapted to measure incident radiation at a plurality of pixels and disposed opposite the source of radiation along a projection line and spaced therefrom to provide a space for the object to be imaged, a mechanism located closer to the radiation source than the imaging device and adapted to vary the source radiation incident upon the imaging device between at least a first band of pixels and a second narrower band of pixels, a scan axis that intersects the projection line and to which an object is aligned in a substantially fixed relationship, a relative rotation between the projection line on the one hand and the scan axis and an object aligned thereto on the other hand, the relative rotation being measured by an angular displacement value, the angular displacement value being effected by a rotation of the projection line with respect to the scan axis, a rotation of the object and the scan axis with respect to the projection line, or both such rotations, the method comprising the steps of:

(a) obtaining a first group of radiographic projections taken by the two-dimensional imaging device at a corresponding first plurality of angular displacement values, the projections of the first group being taken with radiation from the source incident upon a first band of pixels of the imaging device;

(b) obtaining a second group of radiographic projections taken by the two-dimensional imaging device at a corresponding second plurality of angular displacement values, the projections of the second group being taken with the radiation from the source incident upon a second band of pixels of the imaging device, the second band being narrower than the first band;

(c) generating a first set of estimates of the scattered radiation within at least a portion of the second band of pixels for a third plurality of angular displacement values, each estimate of the first set being for a particular angular displacement value of the third plurality and comprising a difference between a first representation of the radiographic projection data taken with the source radiation incident upon the first band of pixels and a second representation of the radiographic projection data taken with the source radiation incident upon the second band of pixels, the first representation being generated from the at least one radiographic projection of the first group, and the second representation being generated from at least one radiographic projection of the second group.

2. The method of claim 1, wherein a first projection from the first group and a second projection from the second group have corresponding angular displacement values that are substantially equal to an angular displacement value of the third plurality, and wherein the estimate for the scattered radiation for said angular displacement value of the third plurality comprises a difference between the first and second projections having substantially the same angular displacement value.

3. The method of claim 1, wherein each estimate of the first set comprises a scatter multiplier that multiplies the difference between the first and second representations, the scatter multiplier being greater than one in value.

4. The method of claim 1, further comprising generating a second set of estimates of the scattered radiation within at least a portion of the second band of pixels for the third plurality of angular displacement values, each estimate of the second set comprising a respective estimate of the first set when the respective estimate of the first set is below a truncated value, and each estimate of the second set comprising the truncated value when the respective estimate of the first set is above the truncated value, the estimate of the second group and the respective estimate of the first group being for the same pixel location and for the same angular displacement value.

5. The method of claim 3, further comprising generating a second set of estimates of the scattered radiation within at least a portion of the second band of pixels for the third plurality of angular displacement values, each estimate of the second set comprising a respective estimate of the first set when the respective estimate of the first set is below a truncated value, and each estimate of the second set comprising the truncated value when the respective estimate of the first set is above the truncated value, the estimate of the second group and the respective estimate of the first group being for the same pixel location and for the same angular displacement value.

6. The method of claim 1, further comprising generating another set of estimates of the scattered radiation within at least a portion of the second band of pixels for the third plurality of angular displacement values, each said estimate comprising a spatial average of a plurality of estimates of the first set for a particular angular displacement value.

7. The method of claim 5, further comprising generating a third set of estimates of the scattered radiation within at least a portion of the second band of pixels for the third plurality of angular displacement values, each estimate of the third set comprising a spatial average of a plurality of estimates of the second set for a particular angular displacement value.

8. The method of claim 7, wherein each estimate of the third set is provided for a row of pixels within the second band, the estimate for the row of pixels being a row estimate for an angular displacement value, and wherein the method further comprises:

assembling the row estimates of the third set into a Sinogram of a spatial dimension versus angular displacement values, the Sinogram being a fourth set of estimates; and generating a fifth set of estimates of the scattered radiation in a Sinogram of the spatial dimension versus angular displacement values, each estimate of the fifth set being for a pixel in the spatial dimension and an angular displacement value and comprising an average of a plurality of estimates of the fourth set that span a plurality of pixels in the spatial dimension and a plurality of pixels in the dimension for angular displacement values.

9. The method of claim 8, wherein the spatial dimension of the Sinogram of the fifth set of estimates corresponds to a first dimension of the two-dimensional imaging device, the imaging device having a second dimension, wherein the method further comprises generating a sixth set of estimates of the scattered radiation for both dimensions of the imaging device and for the third plurality of angular displacement values, each estimate of the sixth set being for the pixels of the imaging device at a particular angular displacement value and comprising a row of the fifth set of estimates in the spatial dimension for the particular angular displacement value multiplied by a scale function, the scale function being a function in the second dimension of the imaging device.

10. The method of claim 1, further comprising generating a second set of estimates of the scattered radiation for a row of pixels within the second band of pixels and for the third plurality of angular displacement values, each said estimate comprising a spatial average of a plurality of estimates of the first set;

assembling the row estimates of the second set into a Sinogram of a spatial dimension versus angular displacement values, the Sinogram being a third set of estimates; and generating a fourth set of estimates of the scattered radiation in a Sinogram of the spatial dimension versus angular displacement values, each estimate of the fourth set being for a pixel in the spatial dimension and an angular displacement value and comprising an average of a plurality of estimates of the third set that span a plurality of pixels in the spatial dimension and a plurality of pixels in the dimension of angular displacement values.

11. The method of claim 10, wherein the spatial dimension of the Sinogram of the fourth set of estimates corresponds to a first dimension of the two-dimensional imaging device, the imaging device having a second dimension, wherein the method further comprises generating a fifth set of estimates of the scattered radiation for both dimensions of the imaging device and for the third plurality of angular displacement values, each estimate of the fifth set being for the pixels of the imaging device at a particular angular displacement value and comprising a row of the fourth set of estimates in the spatial dimension for the particular angular displacement value multiplied by a scale function, the scale function being a function in the second dimension of the imaging device.

12. The method of claim 1, wherein each radiographic projection of the second group obtained by step (b) comprises one or more additional second bands upon which the source radiation is incident;

wherein step (c) further generates an additional first set of estimates within at least a portion of each corresponding additional second band of pixels for the third plurality of angular displacement values, each said estimate comprising a difference between a first representation of the radiographic projection data taken with the source radiation incident upon the first band of pixels and a second representation of the radiographic projection data taken with the source radiation incident upon the additional second band of pixels, the first representation being generated from the at least one radiographic projection of the first group, and the second representation being generated from at least one radiographic projection of the second group;

wherein the method further comprises:

(d) generating, from a respective first set of estimates, a respective second set of estimates of the scattered radiation for a row of pixels within a respective second band of pixels and for the third plurality of angular displacement values, each said estimate of a respective second set comprising a spatial average of a plurality of estimates from the respective first set and being associated with one of the second bands of pixels;

(e) assembling, for each second band of pixels, the row estimates of each associated second set into a Sinogram of a spatial dimension versus angular displacement values, each Sinogram for each second band of pixels being a respective third set of estimates for the respective second band of pixels; and (f) generating, for each second band of pixels, a respective fourth set of estimates of the scattered radiation in a Sinogram of the spatial dimension versus angular displacement values, each fourth set of estimates being generated from the respective third set of estimates assembled for the same second band of pixels, each estimate of a fourth set being for a pixel in the spatial dimension and an angular displacement value and comprising an average of a plurality of estimates of the respective third set that span a plurality of pixels in the spatial dimension and a plurality of pixels in the dimension of angular displacement values, wherein the spatial dimension of the Sinogram of each fourth set of estimates corresponds to a first dimension of the two-dimensional imaging device, the imaging device having a second dimension.

13. The method of claim 12 further comprising:

(g) generating a fifth set of estimates of the scattered radiation for both dimensions of the imaging device and for the third plurality of angular displacement values, each estimate of the fifth set being for the pixels of the imaging device at a particular angular displacement value and comprising a row of one of the fourth set of estimates in the spatial dimension for the particular angular displacement value multiplied by a scale function, the scale function being a function in the second dimension of the imaging device that is generated from the fourth sets of estimates.

14. The method of claim 12 further comprising:

(g) generating a fifth set of estimates of the scattered radiation for both dimensions of the imaging device and for the third plurality of angular displacement values, each estimate of the fifth set being for the pixels of the imaging device at a particular angular displacement value and being generated from at least one curve-fitting function that has the fourth sets of estimates at the particular angular displacement value as inputs.

15. The method of claim 1, wherein the location of the second band in the radiographic projections of the second group varies among a plurality of line locations spanning a first dimension of the imaging device;

wherein the method further comprises:

(d) generating a second set of estimates of the scattered radiation from the first set of estimates, each estimate of the second set being for a row of pixels within a second band of pixels at a particular angular displacement value of the third plurality and comprising a spatial average of a plurality of estimates from the respective first set, the estimate of the second set being associated with the line location of the second band of pixels at the particular angular displacement;

(e) assembling the estimates of the second set having the same associated line location into a respective Sinogram of a spatial dimension versus angular displacement values, each Sinogram for each line location being a respective third set of estimates associated with the line location; and (f) generating for each third set of estimates a respective fourth set of estimates of the scattered radiation in a Sinogram of the spatial dimension versus angular displacement values, each estimate of a fourth set being for a pixel in the spatial dimension and an angular displacement value and comprising an average of a plurality of estimates of the respective third set that span a plurality of pixels in the spatial dimension and a plurality of pixels in the dimension of angular displacement values, each fourth set of estimates being associated with the same line location as the third set of estimates from which it is generated, and wherein the spatial dimension of the Sinogram of each fourth set of estimates corresponds to a first dimension of the two-dimensional imaging device, the imaging device having a second dimension.

16. The method of claim 15 wherein step (e) comprises generating estimates missing at a plurality of angular displacement values by interpolation of estimates at a plurality of other angular displacement values.

17. The method of claim 15 further comprising:

(g) generating a fifth set of estimates of the scattered radiation for both dimensions of the imaging device and for the third plurality of angular displacement values, each estimate of the fifth set being for the pixels of the imaging device at a particular angular displacement value and comprising a row of one of the fourth set of estimates in the spatial dimension for the particular angular displacement value multiplied by a scale function, the scale function being a function in the second dimension of the imaging device that is generated from the fourth sets of estimates.

18. The method of claim 15 further comprising:
(g) generating a fifth set of estimates of the scattered radiation for both dimensions of the imaging device and for the third plurality of angular displacement values, each estimate of the fifth set being for the pixels of the imaging device at a particular angular displacement value and being generated from at least one curve-fitting function that has the fourth sets of estimates at the particular angular displacement value as inputs.

19. A method of reducing the effects of scattered radiation in a particular set of radiographic projections of an object, the information for reducing the effects being collected from the object during a first time period, and the particular set of radiographic projections of the object being taken during a second time period that occurs after the first time period, the initial data and the radiographic projections being generated by a radiation source, a two-dimensional imaging device adapted to measure incident radiation at a plurality of pixels and disposed opposite the source of radiation along a projection line and spaced therefrom to provide a space for the object to be imaged, a mechanism located closer to the radiation source than the imaging device and adapted to vary the source radiation incident upon the imaging device between at least a first band of pixels and a second narrower band of pixels, a scan axis that intersects the projection line and to which an object is aligned in a substantially fixed relationship, a relative rotation between the projection line on the one hand and the scan axis and an object aligned thereto on the other hand, the relative rotation being measured by an angular displacement value, the angular displacement value being effected by a rotation of the projection line with respect to the scan axis, or a rotation of the object and the scan axis with respect to the projection line, or both, the method comprising:
(a) obtaining an initial first group of radiographic projections taken by the two-dimensional imaging device during the first time period, the projections of the initial first group being taken at a corresponding first plurality of angular displacement values, and with radiation from the source incident upon the first band of pixels of the imaging device;
(b) obtaining an initial second group of radiographic projections taken by the two-dimensional imaging device during the first time period, the initial second group of projections being taken at a corresponding second plurality of angular displacement values, and with the radiation from the source incident upon the second band of pixels of the imaging device;
(c) generating a set of estimates of the scattered radiation that may be used to reduce the scattered radiation in the at least one radiographic projection of the initial first group and at least one subsequent first group of radiographic projections, the set of estimates being generated from the initial first group and initial second group of radiographic projections;
(d) obtaining a subsequent first group of radiographic projections taken by the two-dimensional imaging device during the second time period, the projections of the subsequent first group being taken at a corresponding plurality of angular displacement values, and with radiation from the source incident upon substantially the first band of pixels of the imaging device;
(e) generating at least one corrected projection of the subsequent first group of radiographic projections by subtracting estimates of scattered radiation generated for a projection of the subsequent first group by step (e) from that projection of the subsequent first group.

20. The method of claim 19 wherein step (e) comprises the step of aligning the estimates of scattered radiation to said projection of the subsequent first group by comparing data of said projection of the subsequent first group with data of one or more projections of the initial first group.

21. A method of estimating the scattered radiation in a set of radiographic projections of an object, initial data for estimating the scattered radiation being collected from the object during a first time period and the particular set of radiographic projections of an object being taken during a second time period that occurs after the first time period, the initial data and the radiographic projections being generated by a radiation source, a two-dimensional imaging device adapted to measure incident radiation at a plurality of pixels and disposed opposite the source of radiation along a projection line and spaced therefrom to provide a space for the object to be imaged, a mechanism located closer to the radiation source than the imaging device and adapted to vary the source radiation incident upon the imaging device between at least a first band of pixels and a second narrower band of pixels, a scan axis that intersects the projection line and to which an object is aligned in a substantially fixed relationship, a relative rotation between the projection line on the one hand and the scan axis and an object aligned thereto on the other hand, the relative rotation being measured by an angular displacement value, the angular displacement value being effected by a rotation of the projection line with respect to the scan axis, or a rotation of the object and the scan axis with respect to the projection line, or both, the method comprising:
(a) obtaining an initial first group of at least one radiographic projection taken by the two-dimensional imaging device during the first time period, each said projection being taken at a corresponding angular displacement value, and with radiation from the source incident upon a band of pixels of the imaging device that has a width closer to the width of the first band than the width of the second band;
(b) obtaining an initial second group of radiographic projections taken by the two-dimensional imaging device during the first time period, the initial second group of projections being taken at a corresponding second plurality of angular displacement values, and with the radiation from the source incident upon the second band of pixels of the imaging device;
(c) obtaining a subsequent first group of radiographic projections taken by the two-dimensional imaging device during the second time period, the projections of the subsequent first group being taken at a corresponding first plurality of angular displacement values, and with radiation from the source incident upon the first band of pixels of the imaging device;
(d) generating a first set of estimates of the scattered radiation within at least a portion of the second band of pixels for a third plurality of angular displacement values, each estimate of the first set being for a particular angular displacement value of the third plurality and comprising a difference between a first representation of the radiographic projection data taken with the source radiation incident upon the first band of pixels and a second representation of the radiographic projection data taken with the source radiation incident upon the second band of pixels, the first representation being generated from the at least one radiographic projection of the subsequent first group, and the second representation being generated from at least one radiographic projection of the initial second group.

22. The method of claim 21 wherein step (d) comprises the step of aligning the data of the subsequent first group with data of the initial second group by comparing data of the subsequent first group with data of the initial first group.

23. An imaging system comprising:
a controller;
a radiation source;
a two-dimensional imaging device adapted to measure incident radiation at a plurality of pixels and disposed opposite the source of radiation along a projection line and spaced therefrom to provide a space for the object to be imaged, the imaging device being electrically coupled to the controller to provide measured values of the pixels thereto;
a modulator mechanism located closer to the radiation source than the imaging device, the mechanism being responsive to the controller and adapted to vary the source radiation incident upon the imaging device between at least a first band of pixels and a second, narrower band of pixels upon direction from the controller,
a scan axis that intersects the projection line and to which an object is aligned in a substantially fixed relationship;
a gantry that holds the radiation source, the imaging device, and the mechanism in positional relationships to one another;
an object support member;
a relative rotation between the projection line on the one hand and the scan axis and an object aligned thereto on the other hand, the relative rotation being measured by an angular displacement value, the angular displacement value being effected by a rotation of the projection line with respect to the scan axis, a rotation of the object and the scan axis with respect to the projection line, or both such rotations;
a mechanical drive mechanically coupled to at least one of the gantry and the object support member to provide the relative rotation, the mechanical drive being responsive to the controller; and
a set of instructions embodied on a computer readable memory that directs the controller to instruct the mechanical drive to make at least one scan rotation, to direct the modulator mechanism, to read a first group of radiographic projections from the imaging device at a corresponding first plurality of angular displacement values, and to read a second group of radiographic projections from the imaging device at a corresponding second plurality of angular displacement values, the first group of projections being taken with the modulator mechanism set to cause the first band of pixels of the imaging device to be exposed to the source radiation, the second group of projections being taken with the modulator mechanism set to cause the second band of pixels of the imaging device to be exposed to the source radiation.

24. The imaging system of claim 23 wherein the modulator mechanism comprises a pair of fan blades disposed between the radiation source and the imaging device, each fan blade being disposed closer to the radiation source than the imaging device, the fan blades being adjustable to provide a variable gap between their edges, with their edges being disposed on either side of a plane defined by the projection line and the scan axis; and
a fan-blade drive mechanically coupled to the fan blades and responsive to the controller.

25. The imaging system of claim 23 further comprising a set of instructions that direct the processor to generate estimates of the scattered radiation from the first and second groups of projections.

26. The imaging system of claim 23 wherein the center of the imaging device is located on the projection line.

27. The imaging system of claim 23 wherein the center of the imaging device is offset from the projection line.

28. The imaging system of claim 23 wherein the number of projections in the second group is fewer than the number of projections in the first group.

29. A computer program product for directing a data processor to estimate the scattered radiation in radiographic projections of an object, the radiographic projections generated by a radiation source, a two-dimensional imaging device adapted to measure incident radiation at a plurality of pixels and disposed opposite the source of radiation along a projection line and spaced therefrom to provide a space for the object to be imaged, a mechanism located closer to the radiation source than the imaging device and adapted to vary the source radiation incident upon the imaging device between at least a first band of pixels and a second narrower band of pixels, a scan axis that intersects the projection line and to which an object is aligned in a substantially fixed relationship, a relative rotation between the projection line on the one hand and the scan axis and an object aligned thereto on the other hand, the relative rotation being measured by an angular displacement value, the angular displacement value being effected by a rotation of the projection line with respect to the scan axis, a rotation of the object and the scan axis with respect to the projection line, or both such rotations, the computer program product comprising:
a first instruction set that directs the data processor to obtain a first group of radiographic projections taken by the two-dimensional imaging device at a corresponding first plurality of angular displacement values, the projections of the first group being taken with radiation from the source incident upon a first band of pixels of the imaging device;
a second instruction set that directs the data processor to obtain a second group of radiographic projections taken by the two-dimensional imaging device at a corresponding second plurality of angular displacement values, the projections of the second group being taken with the radiation from the source incident upon at least one second band of pixels of the imaging device, each second band being narrower than the first band; and
a third instruction set that directs the data processor to generate a first set of estimates of the scattered radiation within at least a portion of each second band of pixels for a third plurality of angular displacement values, each estimate of the first set being for a particular angular displacement value of the third plurality and for a particular second band and comprising a difference between a first representation of the radiographic projection data taken with the source radiation incident upon the first band of pixels and a second representation of the radiographic projection data taken with the source radiation incident upon the particular second band of pixels, the first representation being generated from the at least one radiographic projection of the first group, and the second representation being generated from at least one radiographic projection of the second group.

30. The computer program product of claim 29 further comprising a fourth instruction set that directs the data processor to generate a second set of estimates of the scattered radiation within at least a portion of each second band of pixels for the third plurality of angular displacement values, each estimate of the second set comprising a respective estimate of the first set when the respective estimate of the first set is below a truncated value, and each estimate of the second set comprising the truncated value when the respective estimate of the first set is above the truncated value, the estimate of the second group and the respective estimate of the first group being for the same pixel location and for the same angular displacement value.

31. The computer program product of claim 30 further comprising a fifth instruction set that directs the data processor to generate a third set of estimates of the scattered radiation for a row of pixels within each second band of pixels for the third plurality of angular displacement values, each estimate of the third set comprising a spatial average of a plurality of estimates of the second set for a particular angular displacement value and particular second band, the estimates for the row of pixels being a row estimate for an angular displacement value and a particular second band.

32. The computer program product of claim 31 further comprising a sixth instruction set that directs the data processor to assemble, for each second band of pixels, the row estimates of each associated third set of estimates into a respective array of a spatial dimension versus angular displacement values, each assembled array being a respective fourth set of estimates of the scattered radiation for the respective second band of pixels, the spatial dimension of the array of each fourth set of estimates corresponding to a first dimension of the two-dimensional imaging device, the imaging device having a second dimension.

33. The computer program product of claim 32 further comprising a seventh instruction set that directs the data processor to generate, for each second band of pixels, a respective fifth set of estimates of the scattered radiation in an array form of the spatial dimension versus angular displacement values, each fifth set of estimates being generated from the respective fourth set of estimates that was assembled for the same second band of pixels, each estimate of the fifth set being for a pixel in the spatial dimension and an angular displacement value and comprising an average of a plurality of estimates of a respective fourth set that span a plurality of pixels in the spatial dimension and a plurality of pixels in the dimension for angular displacement values.

34. The computer program product of claim 33 further comprising an additional instruction set that directs the data processor to generate a sixth set of estimates of the scattered radiation for both dimensions of the imaging device and for the third plurality of angular displacement values, each estimate of the sixth set being for the pixels of the imaging device at a particular angular displacement value and comprising a row of a fifth set of estimates in the spatial dimension for the particular angular displacement value multiplied by a scale function, the scale function being a function in the second dimension of the imaging device.

35. The computer program product of claim 33 further comprising an additional instruction set that directs the data processor to generate a sixth set of estimates of the scattered radiation for both dimensions of the imaging device and for the third plurality of angular displacement values, each estimate of the sixth set being for the pixels of the imaging device at a particular angular displacement value and comprising a row of a fifth set of estimates in the spatial dimension for the particular angular displacement value multiplied by a scale function, the scale function being a function of the second dimension of the imaging device, the additional instruction set comprising a subset of instructions that directs the data processor to generate the scale function from the fifth sets of estimates.

36. The computer program product of claim 33 further comprising an additional instruction set that directs the data processor to generate a sixth set of estimates of the scattered radiation for both dimensions of the imaging device and for the third plurality of angular displacement values, each estimate of the sixth set being for the pixels of the imaging device at a particular angular displacement value and being generated from at least one curve-fitting function that has the fifth sets of estimates at the particular angular displacement value as inputs.

37. The computer program product of claim 29 further comprising a first additional instruction set that directs the data processor to generate a second set of estimates of the scattered radiation for a row of pixels within each second band of pixels for the third plurality of angular displacement values, each estimate of the second set comprising a spatial average of a plurality of estimates of the first set for a particular angular displacement value and particular second band, the estimates for the row of pixels being a row estimate for an angular displacement value and a particular second band.

38. The computer program product of claim 37 further comprising a second additional instruction set that directs the data processor to assemble, for each second band of pixels, the row estimates of each associated second set of estimates into a respective array of a spatial dimension versus angular displacement values, each assembled array being a respective third set of estimates of the scattered radiation for the respective second band of pixels, the spatial dimension of the array of each third set of estimates corresponding to a first dimension of the two-dimensional imaging device, the imaging device having a second dimension.

39. The computer program product of claim 38 further comprising a third additional instruction set that directs the data processor to generate, for each second band of pixels, a respective fourth set of estimates of the scattered radiation in an array form of the spatial dimension versus angular displacement values, each fourth set of estimates being generated from the respective third set of estimates that was assembled for the same second band of pixels, each estimate of the fourth set being for a pixel in the spatial dimension and an angular displacement value and comprising an average of a plurality of estimates of a respective third set that span a plurality of pixels in the spatial dimension and a plurality of pixels in the dimension for angular displacement values.

40. The computer program product of claim 39 further comprising a fourth additional instruction set that directs the data processor to generate a fifth set of estimates of the scattered radiation for both dimensions of the imaging device and for the third plurality of angular displacement values, each estimate of the fifth set being for the pixels of the imaging device at a particular angular displacement value and comprising a row of a fourth set of estimates in the spatial dimension for the particular angular displacement value multiplied by a scale function, the scale function being a function in the second dimension of the imaging device.

41. The computer program product of claim 39 further comprising a fourth additional instruction set that directs the data processor to generate a fifth set of estimates of the scattered radiation for both dimensions of the imaging device and for the third plurality of angular displacement values, each estimate of the fifth set being for the pixels of the imaging device at a particular angular displacement value and comprising a row of a fourth set of estimates in the spatial dimension for the particular angular displacement value multiplied by a scale function, the scale function being a function of the second dimension of the imaging device, the fourth additional instruction set comprising a subset of instructions that directs the data processor to generate the scale function from the fourth sets of estimates.

42. The computer program product of claim 39 further comprising a fourth additional instruction set that directs the data processor to generate a fifth set of estimates of the scattered radiation for both dimensions of the imaging device and for the third plurality of angular displacement values, each estimate of the fifth set being for the pixels of the imaging device at a particular angular displacement value and being generated from at least one curve-fitting function that has the fourth sets of estimates at the particular angular displacement value as inputs.

43. The computer program product of claim 29 wherein the locations of the at least one second band in the radiographic projections of the second group vary among the projections, the locations varying among a plurality of line locations spanning a first dimension of the imaging device, each instance of the at least one second band thereby having a location that varies among a plurality of line locations depending upon the projection, and thus depending upon the angular displacement value for the projection, and wherein the computer program product further comprises:
a first additional instruction set that directs the data processor to generate a second set of estimates of the scattered radiation for a row of pixels within each instance of the at least one second band of pixels for the third plurality of angular displacement values, each estimate of the second set comprising a spatial average of a plurality of estimates of the first set for a particular angular displacement value and particular instance of the at least one second band, the estimates of the second set for the row of pixels providing a row estimate for an angular displacement value and a particular instance of the at least one second band, the row estimate being associated with the line location of the particular instance of the at least one second band from which it is generated; and a second additional instruction set that directs the data processor to assemble the row estimates associated with the same line location into a respective array of a spatial dimension versus angular displacement values, each assembled array being a respective third set of estimates of the scattered radiation for the respective line location, the spatial dimension of the array of each third set of estimates corresponding to a first dimension of the two-dimensional imaging device, the imaging device having a second dimension; and a third additional instruction set that directs the data processor to generate, for each line location, a respective fourth set of estimates of the scattered radiation in an array form of the spatial dimension versus angular displacement values, each fourth set of estimates being generated from the respective third set of estimates that was assembled for the same line location, each estimate of the fourth set being for a pixel in the spatial dimension and an angular displacement value and comprising an average of a plurality of estimates of a respective third set that span a plurality of pixels in the spatial dimension and a plurality of pixels in the dimension for angular displacement values.

44. The computer program product of claim 43 wherein a third set of estimates of the scattered radiation for a respective line location has missing estimated values at a plurality of angular displacement values; and wherein the second additional instruction set comprises instructions that direct the processor to generate the missing estimates by interpolation of estimates at a plurality of other angular displacement values.

45. The computer program product of claim 43 further comprising a fourth additional instruction set that directs the data processor to generate a fifth set of estimates of the scattered radiation for both dimensions of the imaging device and for the third plurality of angular displacement values, each estimate of the fifth set being for the pixels of the imaging device at a particular angular displacement value and comprising a row of one of the fourth set of estimates in the spatial dimension for the particular angular displacement value multiplied by a scale function, the scale function being a function in the second dimension of the imaging device.

46. The computer program product of claim 43 further comprising a fourth additional instruction set that directs the data processor to generate a fifth set of estimates of the scattered radiation for both dimensions of the imaging device and for the third plurality of angular displacement values, each estimate of the fifth set being for the pixels of the imaging device at a particular angular displacement value and comprising a row of one of the fourth set of estimates in the spatial dimension for the particular angular displacement value multiplied by a scale function, the scale function being a function of the second dimension of the imaging device, the fourth additional instruction set comprising a subset of instructions that directs the data processor to generate the scale function from the fourth sets of estimates.

47. The computer program product of claim 43 further comprising a fourth additional instruction set that directs the data processor to generate a fifth set of estimates of the scattered radiation for both dimensions of the imaging device and for the third plurality of angular displacement values, each estimate of the fifth set being for the pixels of the imaging device at a particular angular displacement value and being generated from at least one curve-fitting function that has the fourth sets of estimates at the particular angular displacement value as inputs.

* * * * *